United States Patent
Crooks et al.

(10) Patent No.: US 8,546,415 B2
(45) Date of Patent: Oct. 1, 2013

(54) BIS-PYRIDINO CONTAINING COMPOUNDS FOR THE USE IN THE TREATMENT OF CNS PATHOLOGIES

(75) Inventors: Peter A. Crooks, Nicholasville, KY (US); Linda P. Dwoskin, Lexington, KY (US); Joshua Ayers, Wilmington, DE (US); Vladimir Grinevich, Kernersville, NC (US); Sangeetha Sumithran, Richmond, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 188 days.

(21) Appl. No.: 12/714,219

(22) Filed: Feb. 26, 2010

(65) Prior Publication Data

US 2010/0152237 A1     Jun. 17, 2010

Related U.S. Application Data

(62) Division of application No. 12/219,190, filed on Jul. 17, 2008, now abandoned, which is a division of application No. 11/027,675, filed on Jan. 3, 2005, now abandoned.

(60) Provisional application No. 60/533,213, filed on Dec. 31, 2003.

(51) Int. Cl.
*A61K 31/435*     (2006.01)

(52) U.S. Cl.
USPC ............................................. 514/277

(58) Field of Classification Search
USPC ............................................. 514/277
See application file for complete search history.

(56) References Cited

U.S. PATENT DOCUMENTS

| | | | | |
|---|---|---|---|---|
| 5,776,957 A | * | 7/1998 | Crooks et al. | 514/343 |
| 5,883,094 A | * | 3/1999 | Fliri et al. | 514/242 |
| 5,965,567 A | * | 10/1999 | Archer et al. | 514/282 |
| 6,441,007 B1 | * | 8/2002 | Dull et al. | 514/351 |
| 6,828,349 B1 | * | 12/2004 | Dewey et al. | 514/561 |

FOREIGN PATENT DOCUMENTS

GB     839505     6/1960

OTHER PUBLICATIONS

Ayers et al. "Bis-azaaromatic quaternary ammonium analogues: ligands for .aplph.4beta.2 and .alpha.7 subtypes of neuronal nicotinic receptors" Bioorganic & Medicinal Chemistry Letters, Coden: BMCLE8, vol. 12 No. 21, 2002, pp. 3067-3071 XP002336045.
Broomfield et al., "Binding of soman antidotes to acetylcholine receptors" Biochemical Pharmacology, Coden: BCPCA6, vol. 36, No. 7, 1987, pp. 1017-1022, XP002336046.
Crooks et al., "Development of subtype-selective ligands as antagonists at nicotinic receptors mediating nicotine-evoked dopamine release", Bioorganic & Medicinal Chemistry Letters, Coden: BMCLE8, vol. 14, No. 8, 2004, pp. 1869-1874 XP002336047.
Dwoskin et al., "Subtype-selective nicotinic receptor antagonists: potential as tobacco use cessation agents", Bioorganic & Medicinal Chemistry Letters, Coden: BMCLE8, vol. 14, No. 8, 1863-1867 XP00233604.
Lledos et al., Inorganic Chemistry, 2004, 43, 7622-7635.
Galanakis et al., Journal of Medicinal Chemistry, 1995, 38, 595-606.
Zabicky et al., Macromolecules, 1990, 23, 3755-3762.
Hartwell et al., Journal of the American Chemical Society, 1950, 72, 2040-2044.

* cited by examiner

*Primary Examiner* — John Mabry
(74) *Attorney, Agent, or Firm* — McDermott Will & Emery LLP

(57) ABSTRACT

N-n-Alkylation of nicotine converts nicotine from an agonist into an antagonist specifically for neuronal nicotinic acetylcholine receptor subtypes mediating nicotine-evoked dopamine release. Conformationally restricted analogs exhibit both high affinity and selectivity at this site, and are able to access the brain due to their ability to act as substrates for the blood-brain barrier choline transporter.

16 Claims, 4 Drawing Sheets

FIGURE 1: Compounds of Formula I

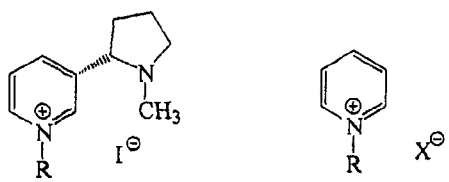
| | | | | | |
|---|---|---|---|---|---|
| 1. | NONI: | R = nC$_8$H$_{17}$ | 4. | NDPI: | R = nC$_{10}$H$_{21}$, X = I |
| 2. | NDNI: | R = nC$_{10}$H$_{21}$ | 5. | NDDPI: | R = nC$_{12}$H$_{25}$, X = I |
| 3. | NDDNI: | R = nC$_{12}$H$_{25}$ | 6. | NPDPB: | R = nC$_{15}$H$_{31}$, X = Br |
| | | | 7. | NEcPB: | R = nC$_{20}$H$_{41}$, X = Br |
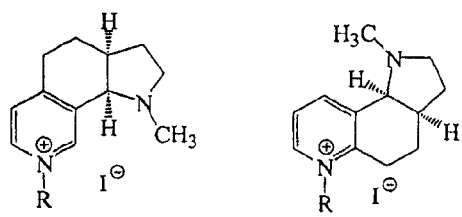
SYN-Series     ANTI-Series
| | | | | | |
|---|---|---|---|---|---|
| 8. | ACO: | R = nC$_8$H$_{17}$ | 13. | BCO: | R = nC$_8$H$_{17}$ |
| 9. | ACN: | R = nC$_9$H$_{19}$ | 14. | BCN: | R = nC$_9$H$_{19}$ |
| 10. | ACD: | R = nC$_{10}$H$_{21}$ | 15. | BCD: | R = nC$_{10}$H$_{21}$ |
| 11. | ACU: | R = nC$_{11}$H$_{23}$ | 16. | BCU: | R = nC$_{11}$H$_{23}$ |
| 12. | ACDD: | R = nC$_{12}$H$_{25}$ | 17. | BCDD: | R = nC$_{12}$H$_{25}$ |
FIGURE 3

18. bNDDB: n=12, X=Br   19. bPDDB: n=12, X=Br

| | | | |
|---|---|---|---|
| NOPiI: | n = 2 | bPiHxI: | n = 4, X = I |
| NDPiI: | n = 4 | bPiOL: | n = 6, X = I |
| NDDPiI: | n = 6 | bPiNB: | n = 7, X = Br |
| | | bPiDI: | n = 8, X = I |
| | | bPiUB: | n = 9, X = Br |
| | | bPiDDB: | n = 10, X = Br |

BIS-PYRIDINO CONTAINING COMPOUNDS FOR THE USE IN THE TREATMENT OF CNS PATHOLOGIES

RELATED APPLICATIONS

This application is a Divisional of U.S. application Ser. No. 12/219,190, filed on Jul. 17, 2008 now abandoned, which is a Divisional of U.S. application Ser. No. 11/027,675, filed Jan. 3, 2005 now abandoned, which claims priority to U.S. Provisional Application Ser. No. 60/533,213, filed Dec. 31, 2003, which is incorporated herein in its entirety.

BACKGROUND OF THE INVENTION

Considerable effort has focused on the development of neuronal nicotinic receptor (nAChR) agonists as therapeutic agents. However, relatively few studies have focused on the therapeutic development of nAChR antagonists. As a result, only a few subtype-selective antagonists are currently available for use as pharmacological tools to investigate the physiological roles of specific nAChR subtypes.

It has been found that nicotine stimulates all known nAChR subtypes, and that N-quaternization of nicotine converts it from an agonist into an antagonist with enhanced nAChR subtype selectivity. Several classical nAChR antagonists are bis-quaternary ammonium structures. Hexamethonium chloride and decamethonium bromide, both bis-quaternary ammonium salts, are considered simplified analogs of d-tubocurarine. The latter drugs have been used to distinguish between peripheral nAChR subtypes, specifically neuromuscular and ganglionic nAChRs. More recently, quaternary ammonium N-n-alkyl analogs of nicotine have been reported to be nAChR subtype-selective antagonists. However, it is generally believed that quaternary ammonium compounds do not easily access the brain due to their charge and polarity. Thus, there remains a need for compounds that are bioavailable in the brain and effective in treatment of nicotine addiction and dopamine mediated disease states.

BRIEF SUMMARY OF THE INVENTION

The present invention is directed to the development and therapeutic use of nAChR subtype-selective and brain-bioavailable antagonists. The compounds are made via modification of the nicotine molecule by (1) quaternization of the pyridine-N atom with a lipophillic substituent to afford N-substituted analogs, and (2) modifying the structure of the nicotinium cationic head group. The compounds of the invention are nicotine antagonists having the formula

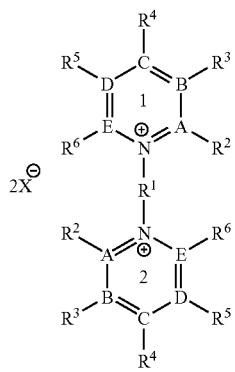

V wherein:
$R^2$, $R^3$, $R^4$, $R^5$, $R^6$ are each independently selected from hydrogen; alkyl; substituted alkyl; cycloalkyl; substituted cycloalkyl, pyrrolidine; N-alkyl pyrrolidine, where the alkyl chain is methyl, ethyl or propyl; unsaturated pyrrolidine; unsaturated N-alkyl pyrrolidine, where the alkyl chain is methyl, ethyl or propyl; aziridine; N-methyl aziridine; azetidine; N-methyl azetidine; unsaturated azetidine; unsaturated N-methyl azetidine; piperidine; N-methyl piperidine; unsaturated piperidine; unsaturated N-methyl piperidine; azepane; N-methyl azepane; unsaturated azepane; unsaturated N-methyl azepane; azocane; N-methyl azocane; unsaturated azocane; unsaturated N-methyl azocane; 1-aza-bicyclo[3.2.1]octane; 1-aza-bicyclo[2.2.1]heptane; 8-methyl-8-aza-bicyclo[3.2.1]octane; 1-aza-tricyclo[3.3.1.1]decane; methyl cycloalkyl; methyl substituted cycloalkyl, methylpyrrolidine; methyl N-alkyl pyrrolidine, where the alkyl chain is methyl, ethyl or propyl; methyl unsaturated pyrrolidine; methyl unsaturated N-alkyl pyrrolidine, where the alkyl chain is methyl, ethyl or propyl; methyl aziridine; methyl N-methyl aziridine; methyl azetidine; methyl N-methyl azetidine; methyl unsaturated azetidine; methyl unsaturated N-methyl azetidine; methyl piperidine; methyl N-methyl piperidine; methyl unsaturated piperidine; methyl unsaturated N-methyl piperidine; methyl azepane; methyl N-methyl azepane; methyl unsaturated azepane; methyl unsaturated N-methyl azepane; methyl azocane; methyl N-methyl azocane; methyl unsaturated azocane; methyl unsaturated N-methyl azocane; methyl 1-aza-bicyclo[3.2.1]octane; methyl 1-aza-bicyclo[2.2.1]heptane; 8-methyl-8-aza-bicyclo[3.2.1]octane; methyl 1-aza-tricyclo[3.3.1.1]decane;

$R^1$ is selected from alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, heterocyclic, substituted heterocyclic, alkoxy, alkylamine, thioalkyl; and X is selected from Cl, Br, I, $HSO_4$, $\frac{1}{2}SO_2$, $CH_3SO_3$, p-TsO, $CF_3SO_3$ and any ion that completes the salt form of the nicotine antagonist; and enantomers, diastereomers and racemic mixes thereof.

The nicotine antagonists of the invention are useful for the treatment of dopamine related conditions and dopamine-mediated disease states such as myasthenia gravis, Parkinson's disease, Alzheimer's disease, schizophrenia, eating disorders, and drug addiction. These compounds are also useful when used as substitutes for psycho-stimulant self-administration. The nicotine antagonists of the invention are particularly useful for treating drug addiction due to nicotinic agonists, cocaine, amphetamines, caffeine, phencyclidine, opiates, barbituates, benzodiazepines, cannabinoids, hallucinogens and alcohol.

The invention further includes a method of treating nicotine addiction by administering a formulation containing one or more compounds of the invention to the patient. The compounds and compositions of the invention may be administered by applying the formulation to a medical patch which is then attached or adhered to the skin of the patient; providing an oral formulation which is taken orally; providing a formulation which is injected into the patient with a syringe or similar device; providing a formulation which is applied to the nasal cavity; providing a formulation which is applied to the rectum; providing a formulation which is inhaled; providing a formulation which is applied sublingual; and any other means of applying the formulation to the patient.

In another aspect of the invention the nicotine antagonists of the invention are administered to a patient in order to inhibit dopamine release from presynaptic terminals in neuronal dopamine tissue in a stereoselective and receptor-mediated manner.

BRIEF DESCRIPTION OF THE DRAWINGS

FIG. 3 shows the chemical structures of N-n-alkylnicotinium (1-3), N-n-alkylpyridinium (4-7), and conformationally restricted N-n-alkylnicotinium (8-17) iodides and bromides.

DETAILED DESCRIPTION OF THE INVENTION

During the development of nAChR receptor antagonists, we discovered that structural modification of the nicotine molecule converted nicotine into a series of N-n-alkylnicotinium analogs exhibiting antagonist activity at specific nAChR subtypes, and several of these antagonists showed both high affinity and subtype-selectivity (Table 4). N-n-Alkylation of nicotine converts nicotine from an agonist into an antagonist at neuronal nicotinic acetylcholine receptor subtypes mediating nicotine-evoked dopamine release. Conformationally restricted analogs exhibit both high affinity and selectivity at this site, and are able to access the brain due to their ability to act as substrates for the blood-brain barrier choline transporter.

Furthermore, when the pyridine-N atom of nicotine is n-alkylated with chain lengths $\geq C_6$, no intrinsic activity at native nAChRs in dopamine release and $^{86}Rb^+$ efflux assays is observed. Moreover, nicotine-evoked dopamine release from striatal slices and nicotine-evoked $^{86}Rb^+$ efflux from thalamic synaptosomes (a functional assay for the $\alpha 4\beta 2^*$ receptor) is inhibited by these analogs.

Figure 1:
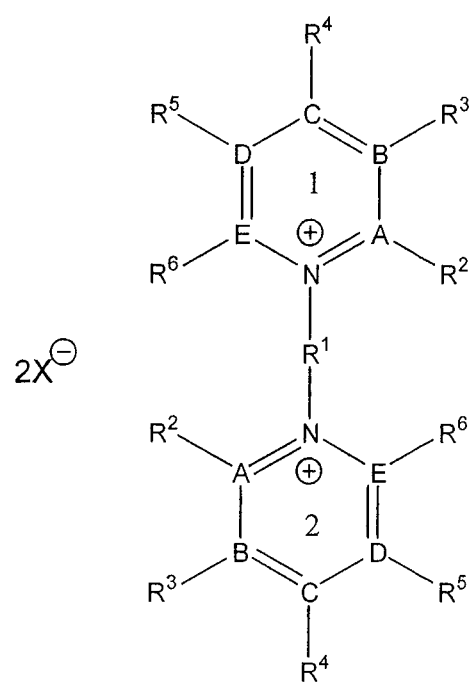
FIG. 1 shows the general chemical structure of the bis-alkyl pyridino compounds of the invention. The identities of R and X groups are described herein.
Figure 2:
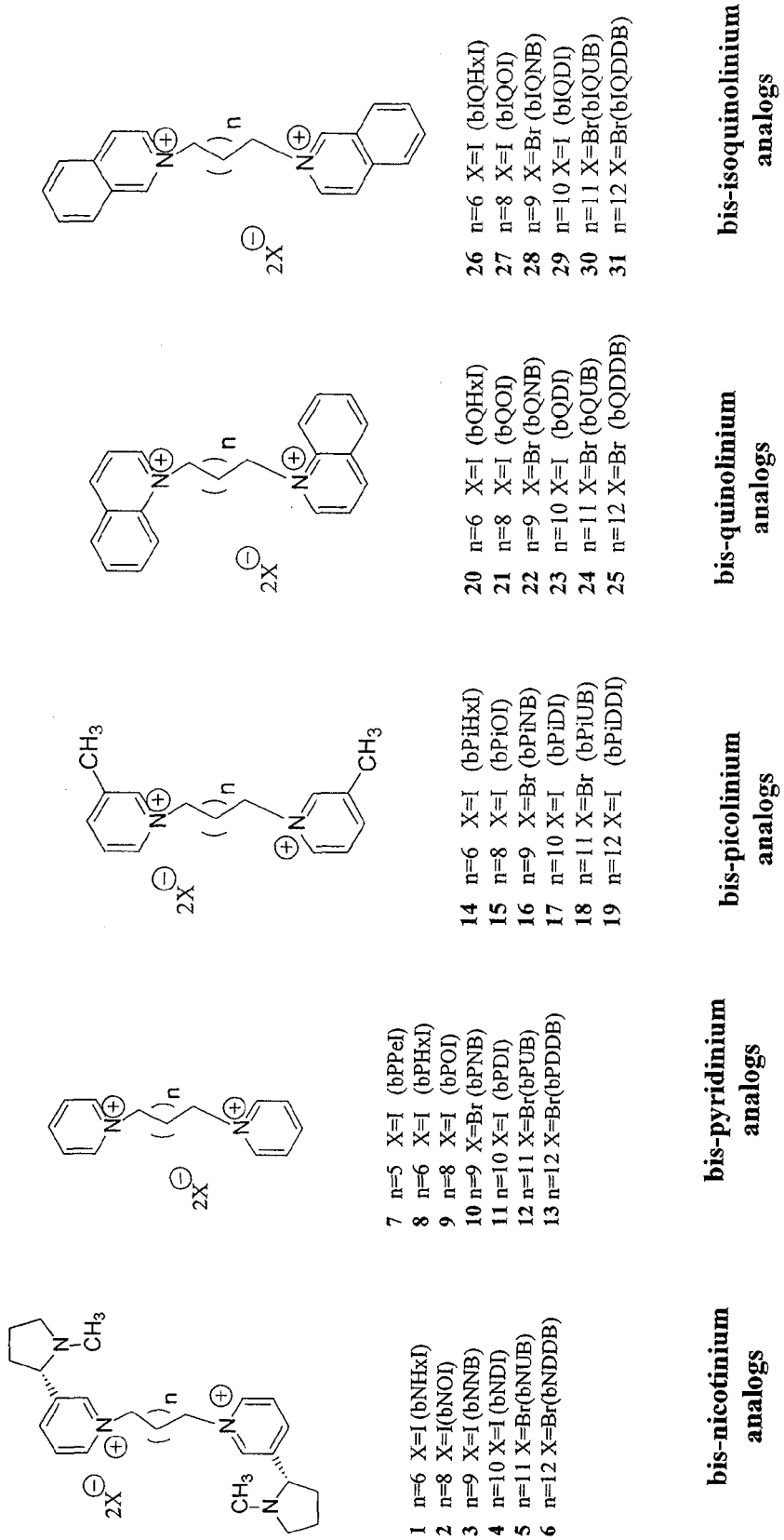
FIG. 2 shows the structures of five series of bis-azaaromatic analogs differentiated by their head groups. The abbreviated nomenclature is given in parentheses.
Figure 4:
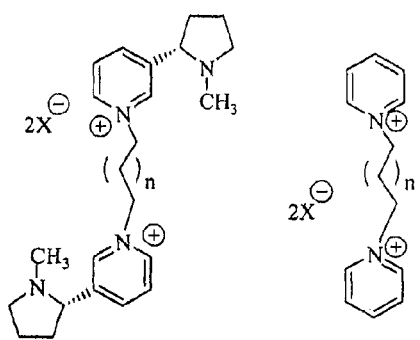
FIG. 4 shows the chemical structures of N,N'-dodecanediyl-bis-nicotinium dibromide (18, bNDDB) and N,N'-dodecanediyl-bis-pyridinium dibromide (19, bPDDB).

The compounds of the present invention are bis-alkyl pyridino compounds corresponding to the chemical structure shown in FIG. 1 (Formula I), wherein:

$R^2$, $R^3$, $R^4$, $R^5$, $R^6$ are each independently selected from hydrogen; alkyl; substituted alkyl; cycloalkyl; substituted cycloalkyl, pyrrolidine; N-alkyl pyrrolidine, where the alkyl chain is methyl, ethyl or propyl; unsaturated pyrrolidine; unsaturated N-alkyl pyrrolidine, where the alkyl chain is methyl, ethyl or propyl; aziridine; N-methyl aziridine; azetidine; N-methyl azetidine; unsaturated azetidine; unsaturated N-methyl azetidine; piperidine; N-methyl piperidine; unsaturated piperidine; unsaturated N-methyl piperidine; azepane; N-methyl azepane; unsaturated azepane; unsaturated N-methyl azepane; azocane; N-methyl azocane; unsaturated azocane; unsaturated N-methyl azocane; 1-aza-bicyclo[3.2.1] octane; 1-aza-bicyclo[2.2.1]heptane; 8-methyl-8-aza-bicyclo[3.2.1]octane; 1-aza-tricyclo[3.3.1.1$^{3,7}$]decane; methyl cycloalkyl; methyl substituted cycloalkyl, methylpyrrolidine; methyl N-alkyl pyrrolidine, where the alkyl chain is methyl, ethyl or propyl; methyl unsaturated pyrrolidine; methyl unsaturated N-alkyl pyrrolidine, where the alkyl chain is methyl, ethyl or propyl; methyl aziridine; methyl N-methyl aziridine; methyl azetidine; methyl N-methyl azetidine; methyl unsaturated azetidine; methyl unsaturated N-methyl azetidine; methyl piperidine; methyl N-methyl piperidine; methyl unsaturated piperidine; methyl unsaturated N-methyl piperidine; methyl azepane; methyl N-methyl azepane; methyl unsaturated azepane; methyl unsaturated N-methyl azepane; methyl azocane; methyl N-methyl azocane; methyl unsaturated azocane; methyl unsaturated N-methyl azocane; methyl 1-aza-bicyclo[3.2.1]octane; methyl 1-aza-bicyclo[2.2.1]heptane; 8-methyl-8-aza-bicyclo[3.2.1]octane; methyl 1-aza-tricyclo[3.3.1.1$^{3,7}$]decane.

$R^1$ is selected from but not limited to, alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, heterocyclic, substituted heterocyclic, alkoxy, alkylamine, thioalkyl; and X is selected from Cl, Br, I, $HSO_4$, $½SO_2$, $CH_3SO_3$, p-TsO or $CF_3SO_3$, or any other ion which would complete the salt form of the compound.

In one embodiment of the present invention, combinations of R groups (i.e., $R_2R_3$, $R_3R_4$, $R_4R_5$, $R_5R_6$) represent a fused aromatic or unsaturated ring Z, where Z includes, but is not limited to, $(CH_2)$ where n=3-8, benzene, pyridine, pyran, indene, isoindene, benzofuran, isobenzofuran, benzo[b]thiophene, benzo[c]thiophene, indole, indolenine, isoindole, cyclopental[b]pyridine, pyrano[3,4-b]pyrrole, indazole, indoxazine, benzosazole, anthranil, naphthalene, tetralin, decalin, chromene, coumarin, chroman-4-one, isocoumarin, isochromen-3-one, quinoline, isoquinoline, cinnoline, quinazoline, naphthyridine, pyrido[3,4-b]-pyridine, pyridol[3,2-b]pyridine, pyrido[4,3,-b]-pyridine, benzoxazine, anthracene, phenanthrene, phenalene, fluorene, carazole, xanthene, acridine, octahydro-[1]pyridine, 1-methyl octahydro-[1]pyridine, octahydro-indole, 1-methyl octahydro-indole, octahydro-cyclopenta[b]pyrrole, 1methyl-octahydro-cyclopenta[b]pyrrole, decahydro-quinoline, 1-methyl-decahydro-quinoline including all possible substitution patterns, geometric and stereoisomers, racemic, diastereomeric and enantiomeric forms thereof.

In certain compounds of the invention, ring 1 and ring 2 are identical or independently an unsaturated nitrogen heterocycle including, but not limited to, pyrrole, pyrrolidine, pyrazole, imidazole, 1,2,3-triazole, 1,2,4-triazole, pyridine, pyridazine, pyrimidine, pyrazine, or triazine, including all possible substitution patterns, geometric and stereoisomers, racemic, diastereomeric and enantiomeric forms thereof.

It is preferred that $R^2$, $R^4$, $R^5$, $R^6$, are individually selected from the group consisting of hydrogen, halogen, alkyl or alkanoyl; $R^3$ is individually selected from the group consisting of hydrogen, halogen, alkyl, alkanoyl, amino, alkylamino, piperidine, N-methyl piperidine, pyrrolidine, N-methylpyrrolidine or quinuclidine; $R^1$ is a branched or non-branched $C_4$-$C_{19}$ alkyl; and X is iodine or bromine.

N,N'-alkyl-bis-picolinium analogs and other bis-azaaromatic analogs were synthesized and assessed in nicotinic receptor (nAChR) assays. Preferred bis-azaaromatic analogs have 6-12 carbon atoms in the alkyl chain, with an even number of carbon atoms in the alkyl chain being preferred to an odd number of carbon atoms, and a longer chain being preferred to a shorter chain. The most potent and subtype-selective analog, N,N'-dodecyl-bis-picolinium bromide (bPiDDB), inhibited nAChRs mediating nicotine-evoked [$^3$H]dopamine release ($IC_{50}$=5 nM; $I_{max}$ of 60%), and did not interact with $\alpha 4\beta 2^*$ or $\alpha 7^*$ nAChRs. Therefore, bPiDDB is the most preferred compound for use as a tobacco use cessation agent and for inhibiting release of dopamine.

The invention includes but is not limited to the use of compounds having the structures shown in FIGS. 1-5, which were prepared by quaternizing the pyridinic nitrogen atom of nicotine with a lipophillic substituent group and modifying the structure of the nicotinium cationic head group.

The invention also includes compositions comprising one or more of the chemical compounds shown in FIGS. 1-5 for use as a tobacco use cessation agent. The most preferred compound for this purpose is N,N'-dodecyl-bis-picolinium bromide (bPiDDB), shown in FIG. 5.

As employed herein, the aforementioned terms are defined as follows:

"lower alkyl" refers to straight or branched chain alkyl radicals having in the range of about 1 up to 4 carbon atoms;

"alkyl" refers to straight or branched chain alkyl radicals having in the range of about 1 up to 19 carbon atoms unless otherwise specified, preferably 1-12 carbon atoms, and more preferably 6-12 carbon atoms, and most preferably 9-12 carbon atoms; and "substituted alkyl" refers to alkyl radicals further bearing one or more substituents such as hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, sulfonamide, and the like.

"Cycloalkyl" refers to cyclic ring-containing radicals containing in the range of about 3 up to 8 carbon atoms and "substituted cycloalkyl" refers to cycloalkyl radicals further bearing one or more substituent as set forth above;

"alkenyl" refers to straight or branched chain hydrocarbyl radicals having at least one carbon-carbon double bond, and having in the range of about 2 up to 19 carbon atoms, preferably 2 to 12 carbon atoms, and more preferably 6 to 12 carbon atoms, and most preferably 9-12 carbon atoms; and "substituted alkenyl" refers to alkenyl radicals further bearing one or more substituents as set forth above;

"alkynyl" refers to straight or branched chain hydrocarbyl radicals having at least one carbon-carbon triple bond, and having in the range of about 2 up to 19 carbon atoms, preferably 2 to 12 carbon atoms, and more preferably 6 to 12 carbon atoms, and most preferably 9-12 carbon atoms; and "substituted alkynyl" refers to alkynyl radicals further bearing one or more substituents as set forth above;

"aryl" refers to aromatic radicals having in the range of about 6 to 24 carbon atoms and "substituted aryl" refers to aryl radicals further bearing one or more substituents as set forth above;

"alkylaryl" refers to alkyl-substituted aryl radicals and "substituted alkylaryl" refers to alkylaryl radicals further bearing one or more substituents as set forth above;

"arylalkyl" refers to aryl-substituted alkyl radicals and "substituted arylalkyl" refers to arylalkyl radicals further bearing one or more substituents as set forth above;

"arylalkenyl" refers to aryl-substituted alkenyl radicals and "substituted arylalkenyl" refers to arylalkenyl radicals further bearing one or more substituents as set forth above;

"arylalkynyl" refers to aryl-substituted alkynyl radicals and "substituted arylalkynyl" refers to arylalkynyl radicals further bearing one or more substituents as set forth above;

"aroyl" refers to aryl-substituted species such as benzoyl and "substituted aroyl" refers to aroyl radicals further bearing one or more substituents as set forth above;

"heterocyclic" refers to cyclic radicals containing one or more heteroatoms as part of the ring structure, and having in the range of 3 up to 24 carbon atoms and "substituted heterocyclic" refers to heterocyclic radicals further bearing one or more substituents as set forth above; "acyl" refers to alkyl-carbonyl species;

"halogen" refers to fluoride, chloride, bromide or iodide radicals; and an "effective amount", when used in reference to compounds of the invention, refers to doses of compound sufficient to provide circulating concentrations high enough to impart a beneficial effect on the recipient thereof. Such levels typically fall in the range of about 0.001 up to 100 mg/kg/day; with levels in the range of about 0.05 up to 10 mg/kg/day being preferred.

The compounds of the invention exhibit various degrees of inhibition of dopamine release from a subset of nicotine receptors. In one embodiment of the invention, a nicotine antagonist of the invention or combination of nicotine antagonisits is administered to a patient in order to inhibit dopamine release from presynaptic terminals in neuronal dopamine tissue in a stereoselective and receptor-mediated manner. The compounds are also able to pass through the blood-brain barrier by accessing the blood-brain barrier choline transporter. Thus, the compounds of the invention are useful in the treatment of smoking addiction and other dopamine-mediated conditions and diseases. Preferred compounds in the treatment of smoking addiction and dopamine-mediated conditions and diseases include:

N,N'-Pentane-1,5-diyl-bis-pyridinium; Diiodide (bPPeI),
N,N'-Hexane-1,6-diyl-bis-pyridinium; Diiodide (bPHxI),
N,N'-Octane-1,8-diyl-bis-pyridinium; Diiodide (bPOI),
N,N'-Nonane-1,9-diyl-bis-pyridinium; Dibromide (bPNB),
N,N'-Decane-1,10-diyl-bis-pyridinium; Diiodide (bPDI),
N,N'-Undecane-1,1'-diyl-bis-pyridinium; Dibromide (bPUB),
N,N'-Dodecane-1,12-diyl-bis-pyridinium; Dibromide (bPDDB),
N,N'-Hexane-1,6-diyl-bis-picolinium; Diiodide (bPiHxI),
N,N'-Octane-1,8-diyl-bis-picolinium; Diiodide (bPiOI),
N,N'-Nonane-1,9-diyl-bis-picolinium; Dibromide (bPiNB),
N,N'-Decane-1,10-diyl-bis-picolinium; Diiodide (bPiDI),
N,N'-Undecane-1,1'-diyl-bis-picolinium; Dibromide (bPiUB),
N,N'-Dodecane-1,12-diyl-bis-picolinium; Dibromide (bPiDDB),
N,N'-Hexane-1,6-diyl-bis-quinolinium; Diiodide (bQHxI),
N,N'-Octane-1,8-diyl-bis-quinolinium; Diiodide (bQOI),
N,N'-Nonane-1,9-diyl-bis-quinolinium; Dibromide (bQNB),
N,N'-Decane-1,10-diyl-bis-quinolinium; Diiodide (bQDI),
N,N'-Undecane-1,1'-diyl-bis-quinolinium; Dibromide (bQUB),
N,N'-Dodecane-1,12-diyl-bis-quinolinium; Dibromide (bQDDB),
N,N'-Hexane-1,6-diyl-bis-isoquinolinium; Diiodide (bIQHxI),
N,N'-Octane-1,8-diyl-bis-isoquinolinium; Diiodide (bIQOI),
N,N'-Nonane-1,9-diyl-bis-isoquinolinium; Dibromide (bIQNB),
N,N'-Decane-1,10-diyl-bis-isoquinolinium; Diiodide (bIQDI),
N,N'-Undecane-1,1'-diyl-bis-isoquinolinium; Dibromide (bIQUB),
N,N'-Dodecane-1,12-diyl-bis-isoquinolinium; Dibromide (bIQDDB),
N,N'-Hexane-1,6-diyl-bis-nicotinium; Diiodide (bNHxI),
N,N'-Octane-1,8-diyl-bis-nicotinium; Diiodide (bNOI),
N,N'-Nonane-1,9-diyl-bis-nicotinium; Dibromide (bNNB),
N,N'-Decane-1,10-diyl-bis-nicotinium; Diiodide (bNDI),
N,N'-Undecane-1,1'-diyl-bis-nicotinium; Dibromide (bNUB),
N,N'-Dodecane-1,12-diyl-bis-nicotinium; Dibromide (bNDDB).

The compounds of the invention can be prepared from corresponding free bases by reaction with an appropriate alkyl iodide using techniques known to those skilled in the art of organic synthesis.

The nicotine antagonists of Formula I include all possible diastereomers and all enantiomeric forms as well as racemic mixtures. The compounds can be separated into substantially optically pure compounds. The compounds of the invention are nicotinic receptor agents, which inhibit [$^3$H]nicotine binding and [$^3$H]MLA binding and nicotine-evoked [$^3$H]DA release from a subset of nACh receptors that mediate nicotine-evoked dopamine release. Thus, the compounds of the invention are useful in treatment of dopamine mediated diseases, such as myasthenia gravis, Parkinson's disease, Alzheimer's disease, schizophrenia, eating disorders, and drug addiction. The compounds may also be used as substitutes for psycho-stimulant self-administration.

The nicotine antagonists of the invention can be administered in any useful form, such as orally, transdermally, transnasally, rectally, sublinguinally, subdermally, intraocularly and via inhalation smokeless delivery. In general, an effective amount of the nicotine antagonist ranges from about). 1 to about 50 mg per kg of body weight, preferably about 0.2 to about 35 mg per kg of body weight. The compound or combination of compounds can be administered as needed, such as once daily or between one and three times daily, for example.

The effects of the compounds of the invention on inhibition of nicotine-evoked dopamine release is striking, in that inhibitory potency is linearly related to n-alkyl chain length. Thus, the greater the number of carbons in the n-alkyl chain, the greater the potency (i.e., the lower the $IC_{50}$ value) for inhibition of nicotine-evoked [$^3$H]-dopamine overflow. Compounds bearing n-alkyl groups from $C_1$ to $C_4$ are low potency antagonists ($IC_{50}$>10 μM); the most potent compound is the $C_{12}$ analog, NDDNI ($IC_{50}$=9 nM) (Table 1), indicating that a relatively long n-alkyl chain provides potent inhibition. Therefore, analogs with alkyl chain lengths of 6 to 12 carbon atoms are preferred, and analogs with alkyl chain lengths of 9 to 12 carbon atoms are more preferred. Analogs with chain lengths greater than $C_{12}$ are less preferred, due to poor water solubility. In the regression analysis of linearity between n-alkyl chain length and inhibitory activity, an orderly progression in potency from $C_1$ (NMNI) to $C_{12}$ (NDDNI) is observed, with the exception of the n-decyl analog, NDNI, which unexpectedly does not exhibit inhibitory activity at the nAChR subtype mediating nicotine-evoked dopamine release (Table 1). NDNI is believed to exist in solution in a unique conformation that is different from the conformations of the other N-n-alkylnicotinium analogs.

The most potent antagonists in this series of analogs produce 80-100% maximal inhibition of the response to nicotine. Thus, these N-n-alkylnicotinium analogs represent a new class of nAChR antagonist, and the most potent compound, NDDNI, is at least two orders of magnitude more potent than the classical antagonist, dihydro-β-erthyroidine (DHβE) as an inhibitor of nAChRs mediating nicotine-evoked dopamine release. In addition, kinetic studies (Schild analysis) indicate that the $C_8$ compound, NONI interacts in a competitive manner with these receptors.

Unlike agonist molecules, antagonists which are generally larger molecules, have been proposed to dock onto the agonist-binding site, but extend beyond the region of agonist binding. The additional structural bulk associated with antagonist molecules has been proposed to prevent the receptor protein from achieving the open channel form. In this respect, the active N-n-alkylnicotinium analogs are of significantly larger molecular weight than nicotine, and the sterically bulky N-n-alkyl chain may interact within a hydrophobic cavity extending outside the normal volume for agonist binding to the receptor. N-n-Alkylnicotinium analogs have been proposed to interact with the nAChR mediating nicotine-evoked dopamine release in the unprotonated form, leading to a reversal in the role of the pharmacophoric N-containing moieties. Thus, the quaternary pyridinium N-atom of the antagonist molecule is believed to interact with the binding site that normally accommodates the protonated pyrrolidine N-atom in the agonist binding mode, and the unprotonated pyrrolidine N-atom of the antagonist molecule substitutes for the pyridine N-atom of the agonist molecule at the hydrogen-bonding site of the nAChR. Alternatively, these N-n-alkylnicotinium molecules may interact with the nicotine binding site in a manner allowing free positioning of the n-alkyl chain into the receptor ion channel, thereby sterically inhibiting ion flux through the channel.

The N-n-alkylnicotinium analogs of the invention have also been evaluated for their affinity for α4β2* and α7* nAChRs. These compounds generally exhibit low affinity for α7* nAChRs. In addition, these N-n-alkylnicotinium analogs exhibit affinity for [$^3$H]-nicotine binding sites across a ~200-fold concentration range, from ~90 nM (NDNI) to ~20 μM (NONI). A simple linear relationship is observed between the length of the n-alkyl chain and affinity for the [$^3$H]-nicotine binding site, with the exception of the $C_8$ analog, NONI. Thus, analogs with longer chain lengths ($C_9$, $C_{10}$ and $C_{12}$) generally are more potent inhibitors than analogs with shorter chain lengths ($C_1$-$C_7$). Higher affinity of longer n-alkyl chain analogs for [$^3$H]-nicotine binding sites may reflect a stronger association with the nAChR due to an increased lipophilic interaction of the carbon chain with a region of the protein near the [$^3$H]-nicotine binding pocket, likely rich in hydrophobic amino acid residues. Thus, the lipophilic interaction may stabilize the analog-receptor complex, increasing the inhibitory potency of longer chain analogs.

Scatchard analyses of [$^3$H]-nicotine saturation binding in the absence and presence of NONI and NDNI indicate that affinity for [$^3$H]-nicotine binding sites decreases in the presence of increasing concentrations of either NDNI or NONI, with no change in $B_{max}$ value, indicating that these compounds interact with the high affinity [$^3$H]-nicotine binding site in a competitive manner, suggesting interaction with specific amino acid residues involved in [$^3$H]-nicotine binding or with nearby residues allowing for steric hindrance of [$^3$H]-nicotine binding.

The high affinity of NONI to inhibit nicotine-evoked [$^3$H]-dopamine release from superfused striatal slices and its low affinity for the [$^3$H]-nicotine and [$^3$H]-methyllycaconitine binding sites, indicate that NONI has selectivity for nAChR subtypes mediating nicotine-evoked dopamine release in striatum. The high affinity of NDNI combined with its lack of affinity for the [$^3$H]-methyllycaconitine binding sites and its lack of inhibition of nicotine-evoked [$^3$H]-dopamine release from superfused rat striatal slices, indicates that NDNI has selectivity for α4β2* nAChRs. Thus, N-n-alkylnicotinium analogs are useful ligands for defining structural topographies of recognition sites of nAChR subtypes through computer-assisted modeling.

The invention will now be described in greater detail by reference to the following non-limiting examples.

Example 1

N,N'-Pentane-1,5-diyl-bis-pyridinium Diiodide (bPPeI)

1,5-Diiodopentane (mmol) was added to a solution (30 mL) of dry pyridine, and the solution heated for 24 hours at 65° C. The resulting precipitate was filtered, and the product washed five times with dry diethyl ether. The resulting yellow solid was isolated in a 90% yield. $^1$H NMR (300 MHz, DMSO-D$_6$) δ 9.14 (2H, d, C2&C6-H), 8.62 (1H, t, C4-H), 8.19 (2H, t, C3&C5-H), 4.62 (2H, t, C'1-CH$_2$), 1.92 (2H, m, C'2-CH$_2$), 1.25 (1H, m, C'3-CH$_2$).

Example 2

N,N'-Hexane-1,6-diyl-bis-pyridinium Diiodide
(bPHxI)

1,6-Diiodohexane (mmol) was added to a solution (30 mL) of dry pyridine, and the solution heated for 24 hours at 65° C. The resulting precipitate was filtered, and the product washed five times with dry diethyl ether. The resulting yellow solid was isolated. $^1$H NMR (300 MHz, DMSO-D$_6$) δ 9.11 (2H, d, C2&C6-H), 8.63 (1H, t, C4-H), 8.18 (2H, t, C3&C5-H), 4.59 (2H, t, C'1-CH$_2$), 1.89 (2H, m, C'2-CH$_2$), 1.28 (2H, m, C'3-CH$_2$).

Example 3

N,N'-Octane-1,8-diyl-bis-pyridinium Diiodide
(bPOI)

1,8-Diiodooctane (mmol) was added to a solution (30 mL) of dry pyridine, and the solution heated for 24 hours at 65° C. The resulting precipitate was filtered, and the product washed five times with dry diethyl ether. The resulting yellow solid was isolated in a 93% yield. $^1$H NMR (300 MHz, DMSO-D$_6$) δ 9.11 (2H, d, C2&C6-H), 8.63 (1H, t, C4-H), 8.18 (2H, t, C3&C5-H), 4.59 (2H, t, C'1-CH$_2$), 1.89 (2H, m, C'2-CH$_2$), 1.28 (4H, m, C'3&4-CH$_2$); $^{13}$C NMR (75 MHz, DMSO-D$_6$) δ 145.3, 144.5, 127.9, 60.5, 30.6, 28.1, 25.2.

Example 4

N,N'-Nonane-1,9-diyl-bis-pyridinium Dibromide
(bPNB)

1,9-Dibromononane (mmol) was added to a solution (30 mL) of dry pyridine, and the solution heated for 24 hours at 65° C. The resulting precipitate was filtered, and the product washed five times with dry diethyl ether. The resulting clear liquid was isolated in a 87% yield. $^1$H NMR (300 MHz, DMSO-D$_6$) δ 9.17 (2H, d, C2&C6-H), 8.61 (1H, t, C4-H), 8.18 (2H, t, C3&C5-H), 4.63 (2H, t, C'1-CH$_2$), 1.89 (2H, m, C'2-CH$_2$), 1.22 (5H, m, C'3-5-CH$_2$); $^{13}$C NMR (75 MHz, DMSO-D$_6$) δ 145.3, 144.5, 127.9, 60.5, 30.7, 28.4, 28.2, 25.3.

Example 5

N,N'-Decane-1,10-diyl-bis-pyridinium Diiodide
(bPDI)

1,10-Diiodododecane (mmol) was added to a solution (30 mL) of dry pyridine, and the solution heated for 24 hours at 65° C. The resulting precipitate was filtered, and the product washed five times with dry diethyl ether. The resulting yellow solid was isolated in a 90% yield. $^1$H NMR (300 MHz, DMSO-D$_6$) δ 9.10 (2H, d, C2&C6-H), 8.63 (1H, t, C4-H), 8.19 (2H, t, C3&C5-H), 4.60 (2H, t, C'1-CH$_2$), 1.89 (2H, m, C'2-CH$_2$), 1.24 (6H, m, C'3-5-CH$_2$); $^{13}$C NMR (75 MHz, DMSO-D$_6$) δ 145.3, 144.5, 127.9, 60.6, 30.6, 28.8, 28.1, 25.2.

Example 6

N,N'-Undecane-1,1'-diyl-bis-pyridinium Dibromide
(bPUB)

1,11-Dibromoundecane (mmol) was added to a solution (30 mL) of dry pyridine, and the solution heated for 24 hours at 65° C. The resulting precipitate was filtered, and the product washed five times with dry diethyl ether. The resulting tan liquid was isolated in a 91% yield. $^1$H NMR (300 MHz, DMSO-D$_6$) δ 9.18 (2H, d, C2&C6-H), 8.62 (1H, t, C4-H), 8.19 (2H, t, C3&C5-H), 4.63 (2H, t, C'1-CH$_2$), 1.88 (2H, m, C'2-CH$_2$), 1.22 (7H, m, C'3-6-CH$_2$).

Example 7

N,N'-Dodecane-1,12-diyl-bis-pyridinium Dibromide
(bPDDB)

1,12-Dibromododecane (mmol) was added to a solution (30 mL) of dry pyridine, and the solution heated for 24 hours at 65° C. The resulting precipitate was filtered, and the product washed five times with dry diethyl ether. The resulting white solid was isolated in a 93% yield. $^1$H NMR (300 MHz, DMSO-D$_6$) δ 9.15 (2H, d, C2&C6-H), 8.62 (1H, t, C4-H), 8.19 (2H, t, C3&C5-H), 4.61 (2H, t, C'1-CH$_2$), 1.88 (2H, m, C'2-CH$_2$), 1.22 (8H, m, C'3-6-CH$_2$); $^{13}$C NMR (75 MHz, DMSO-D$_6$) δ 145.3, 144.6, 127.9, 60.7, 30.8, 28.9, 28.8, 28.5, 25.4.

Example 8

N,N'-Hexane-1,6-diyl-bis-quinolinium Diiodide
(bQHxI)

1,6-Diiodohexane (mmol) was added to a solution (30 mL) of dry quinoline, and the solution heated for 24 hours at 65° C. The resulting precipitate was filtered, and the product washed five times with dry diethyl ether. The resulting yellow solid was isolated. $^1$H NMR (300 MHz, DMSO-D$_6$) δ 9.53 (1H, d, C2-H), 9.29 (1H, d, C3-H), 8.61 (1H, d, C8-H), 8.50 (1H, d, C4-H), 8.29 (1H, t, C7-H), 8.18 (1H, t, C5-H), 8.07 (1H, d, C6-H), 5.09 (2H, t, C'1-CH$_2$), 1.96 (2H, m, C'2-CH$_2$), 1.25 (2H, m, C'3-CH$_2$).

Example 9

N,N'-Octane-1,8-diyl-bis-quinolinium Diiodide
(bQOI)

1,8-Diiodooctane (mmol) was added to a solution (30 mL) of dry quinoline, and the solution heated for 24 hours at 65° C. The resulting precipitate was filtered, and the product washed five times with dry diethyl ether. The resulting yellow solid was isolated in an 89% yield. $^1$H NMR (300 MHz, DMSO-D$_6$) δ 9.53 (1H, d, C2-H), 9.29 (1H, d, C3-H), 8.61 (1H, d, C8-H), 8.50 (1H, d, C4-H), 8.29 (1H, t, C7-H), 8.18 (1H, t, C5-H), 8.07 (1H, d, C6-H), 5.09 (2H, t, C'1-CH$_2$), 1.96 (2H, m, C'2-CH$_2$), 1.25 (4H, m, C'3&4-CH$_2$); $^{13}$C NMR (75 MHz, DMSO-D$_6$) δ 149.5, 147.4, 137.4, 135.6, 130.7, 129.9, 129.7, 122.1, 118.9, 57.3, 29.5, 28.5, 25.7.

Example 10

N,N'-Nonane-1,9-diyl-bis-quinolinium Dibromide
(bQNB)

1,9-Dibromononane (mmol) was added to a solution (30 mL) of dry quinoline, and the solution heated for 24 hours at 65° C. The resulting precipitate was filtered, and the product washed five times with dry diethyl ether. The resulting purple solid was isolated in a 92% yield. $^1$H NMR (300 MHz, DMSO-D$_6$) δ 9.68 (1H, d, C2-H), 9.34 (1H, d, C3-H), 8.67 (1H, d, C8-H), 8.55 (1H, d, C4-H), 8.27 (2H, m, C5&C7-H), 8.07 (1H, d, C6-H), 5.09 (2H, t, C'1-CH$_2$), 1.95 (2H, m, C'2-CH$_2$), 1.19-1.45 (5H, m, C'3-5-CH$_2$).

Example 11

N,N'-Decane-1,10-diyl-bis-quinolinium Diiodide (bQDI)

1,10-Diiododecane (mmol) was added to a solution (30 mL) of dry quinoline, and the solution heated for 24 hours at 65° C. The resulting precipitate was filtered, and the product washed five times with dry diethyl ether. The resulting yellow solid was isolated in a 91% yield. $^1$H NMR (300 MHz, DMSO-D$_6$) δ 9.53 (1H, d, C2-H), 9.29 (1H, d, C3-H), 8.61 (1H, d, C8-H), 8.50 (1H, d, C4-H), 8.29 (1H, t, C7-H), 8.18 (1H, t, C5-H), 8.06 (1H, d, C6-H), 5.04 (2H, t, C'1-CH$_2$), 1.96 (2H, m, C'2-CH$_2$), 1.32 (6H, m, C'3-5-CH$_2$); $^{13}$C NMR (75 MHz, DMSO-D$_6$) δ 149.5, 147.4, 137.4, 135.6, 130.7, 129.9, 129.7, 122.1, 118.9, 57.3, 29.5, 28.9, 28.5, 25.7.

Example 12

N,N'-Undecane-1,1'-diyl-bis-quinolinium Dibromide (bQUB)

1,11-Dibromoundecane (mmol) was added to a solution (30 mL) of dry quinoline, and the solution heated for 24 hours at 65° C. The resulting precipitate was filtered, and the product washed five times with dry diethyl ether. The resulting purple solid was isolated in a 87% yield. $^1$H NMR (300 MHz, CDCl$_3$) δ 9.54 (1H, d, C2-H), 9.28 (1H, d, C3-H), 8.60 (1H, d, C8-H), 8.48 (1H, d, C4-H), 8.27 (1H, t, C7-H), 8.16 (1H, t, C5-H), 8.05 (1H, d, C6-H), 5.03 (2H, t, C'1-CH$_2$), 1.95 (2H, m, C'2-CH$_2$), 1.15-1.48 (7H, m, C'3-6-CH$_2$); $^{13}$C NMR (75 MHz, DMSO-d$_6$) δ 149.5, 147.4, 137.4, 135.6, 130.7, 129.9, 129.7, 122.1, 118.9, 57.3, 29.5, 28.9, 28.8, 28.5, 25.7.

Example 13

N,N'-Dodecane-1,12-diyl-bis-quinolinium Dibromide (bQDDB)

1,12-Dibromododecane (mmol) was added to a solution (30 mL) of dry quinoline, and the solution heated for 24 hours at 65° C. The resulting precipitate was filtered, and the product washed five times with dry diethyl ether. The resulting yellow solid was isolated in a 92% yield. $^1$H NMR (300 MHz, DMSO-D$_6$) δ 9.58 (1H, d, C2-H), 9.29 (1H, d, C3-H), 8.61 (1H, d, C8-H), 8.50 (1H, d, C4-H), 8.29 (1H, t, C7-H), 8.18 (1H, t, C5-H), 8.04 (1H, d, C6-H), 5.04 (2H, t, C'1-CH$_2$), 1.95 (2H, m, C'2-CH$_2$), 1.2-1.4 (8H, m, C'3-6-CH$_2$); $^{13}$C NMR (75 MHz, DMSO-D$_6$) δ 149.5, 147.4, 137.4, 135.6, 130.7, 129.9, 129.7, 122.1, 118.9, 57.3, 29.5, 28.9, 28.8, 28.5, 25.7.

Example 14

N,N'-Hexane-1,6-diyl-bis-picolinium Diiodide (bPiOI)

1,6-Diiodohexane (mmol) was added to a solution (30 mL) of 3-picoline, and the solution heated for 24 hours at 65° C. The resulting precipitate was filtered, and the product washed five times with dry diethyl ether. The precipitate was then dissolved in water (30 mL) and extracted with chloroform (3×30 mL). The aqueous layer was collected and evaporated to dryness on a rotary evaporator. The resulting pale yellow solid was isolated. $^1$H NMR (300 MHz, DMSO-D$_6$) δ 9.03 (1H, s, C2-H), 8.93 (1H, d, C6-H), 8.46 (1H, d, C4-H), 8.08 (1H, t, C5-H), 4.55 (2H, t, C'1-CH$_2$), 2.74 (3H, s, C3-CH$_3$), 2.13 (2H, m, C'2-CH$_2$), 1.46 (2H, m, C'3-CH$_2$).

Example 15

N,N'-Octane-1,8-diyl-bis-picolinium Diiodide (bPiOI)

1,8-Diiodooctane (mmol) was added to a solution (30 mL) of 3-picoline, and the solution heated for 24 hours at 65° C. The resulting precipitate was filtered, and the product washed five times with dry diethyl ether. The precipitate was then dissolved in water (30 mL) and extracted with chloroform (3×30 mL). The aqueous layer was collected and evaporated to dryness on a rotary evaporator. The resulting pale yellow solid was isolated in a 94% yield. $^1$H NMR (300 MHz, DMSO-D$_6$) δ 9.18 (1H, s, C2-H), 8.96 (1H, d, C6-H), 8.46 (1H, d, C4-H), 8.07 (1H, t, C5-H), 4.62 (2H, t, C'1-CH$_2$), 2.50 (3H, s, C3-CH$_3$), 1.94 (2H, m, C'2-CH$_2$), 1.27 (4H, m, C'3&4-CH$_2$); $^{13}$C NMR (75 MHz, DMSO-D$_6$) δ 145.5, 143.9, 141.7, 138.5, 127.1, 60.4, 30.5, 28.1, 25.2, 17.9.

Example 16

N,N'-Nonane-1,9-diyl-bis-picolinium Dibromide (bPiNB)

1,9-Dibromononane (mmol) was added to a solution (30 mL) of 3-picoline, and the solution heated for 24 hours at 65° C. The resulting precipitate was filtered, and the product washed five times with dry diethyl ether. The precipitate was then dissolved in water (30 mL) and extracted with chloroform (3×30 mL). The aqueous layer was collected and evaporated to dryness on a rotary evaporator. The resulting tan liquid was isolated in a 90% yield. $^1$H NMR (300 MHz, DMSO-D$_6$) δ 9.17 (1H, s, C2-H), 9.04 (1H, d, C6-H), 8.47 (1H, d, C4-H), 8.08 (1H, t, C5-H), 4.60 (2H, t, C'1-CH$_2$), 2.50 (3H, s, C3-CH$_3$), 1.92 (2H, m, C'2-CH$_2$), 1.27 (5H, m, C'3-5-CH$_2$); $^{13}$C NMR (75 MHz, DMSO-D$_6$) δ 145.5, 144.1, 141.8, 138.5, 127.1, 60.4, 30.7, 28.5, 28.3, 25.4, 17.9.

Example 17

N,N'-Decane-1,10-diyl-bis-picolinium Diiodide (bPiDI)

1,10-Diiododecane (mmol) was added to a solution (30 mL) of 3-picoline, and the solution heated for 24 hours at 65° C. The resulting precipitate was filtered, and the product washed five times with dry diethyl ether. The precipitate was then dissolved in water (30 mL) and extracted with chloroform (3×30 mL). The aqueous layer was collected and evaporated to dryness on a rotary evaporator. The resulting off white solid was isolated in a 92% yield. $^1$H NMR (300 MHz, CDCl$_3$) δ 9.04 (1H, s, C2-H), 8.94 (1H, d, C6-H), 8.46 (1H, d, C4-H), 8.06 (1H, t, C5-H), 4.58 (2H, t, C'1-CH$_2$), 2.50 (3H, s, C3-CH$_3$), 1.90 (2H, m, C'2-CH$_2$), 1.27 (6H, m, C'3-5-CH$_2$).

Example 18

N,N'-Undecane-1,1'-diyl-bis-picolinium Dibromide (bPiUB)

1,11-Dibromoundecane (mmol) was added to a solution (30 mL) of 3-picoline, and the solution heated for 24 hours at 65° C. The resulting precipitate was filtered, and the product washed five times with dry diethyl ether. The precipitate was then dissolved in water (30 mL) and extracted with chloroform (3×30 mL). The aqueous layer was collected and evaporated to dryness on a rotary evaporator. The resulting tan liquid was isolated in a 90% yield. $^1$H NMR (300 MHz, DMSO-$D_6$) δ 9.10 (1H, s, C2-H), 8.98 (1H, d, C6-H), 8.46 (1H, d, C4-H), 8.07 (1H, t, C5-H), 4.58 (2H, t, C'1-$CH_2$), 2.50 (3H, s, C3-$CH_3$), 1.90 (2H, m, C'2-$CH_2$), 1.26 (7H, m, C'3-6-$CH_2$); $^{13}$C NMR (75 MHz, DMSO-$D_6$) δ 145.5, 144.0, 141.8, 138.5, 127.1, 60.5, 30.7, 28.8, 28.7, 28.4, 25.4, 17.9.

Example 19

N,N'-Dodecane-1,12-diyl-bis-picolinium Dibromide (bPiDDB)

1,12-Dibromododecane (mmol) was added to a solution (30 mL) of 3-picoline, and the solution heated for 24 hours at 65° C. The resulting precipitate was filtered, and the product washed five times with dry diethyl ether. The precipitate was then dissolved in water (30 mL) and extracted with chloroform (3×30 mL). The aqueous layer was collected and evaporated to dryness on a rotary evaporator. The resulting tan liquid was isolated in a 92% yield. $^1$H NMR (300 MHz, $CDCl_3$) δ 9.04 (1H, s, C2-H), 8.94 (1H, d, C6-H), 8.46 (1H, d, C4-H), 8.16 (1H, t, C5-H), 4.55 (2H, t, C'1-$CH_2$), 2.50 (3H, s, C3-$CH_3$), 1.90 (2H, m, C'2-$CH_2$), 1.25 (8H, m, C'3-6-$CH_2$).

Example 20

N,N'-Hexane-1,6-diyl-bis-nicotinium Diiodide (bNHxI)

S-(−)-Nicotine (30.8 mmol) was dissolved in glacial acetic acid (35 mL) and the solution was stirred at ambient temperature for 5 minutes. 1,6-Diiodohexane (15.4 mmol) was added to the solution and the mixture stirred and refluxed for 3 days. The mixture was then evaporated under reduced pressure to remove the solvent and the resulting oil was treated with an aqueous mixture of sodium bicarbonate. The aqueous mixture was extracted with ethyl ether (3×50 mL) and chloroform (3×50 mL) and the aqueous layer collected and was evaporated to dryness on a rotary evaporator, and the resulting solid was treated with chloroform and filtered. The filtrate was collected and evaporated to dryness. The resulting yellow oil was isolated. $^1$H NMR (300 MHz, $CDCl_3$), δ 9.44 (1H, s, C2-H), 9.38 (1H, d, C6-H), 8.44 (1H, d, C4-H), 8.13 (1H, m. C3-H), 4.95 (2H, t, C"1-$CH_2$), 4.03 (1H, t, pyrrolidine $CH_2$), 3.25 (1H, t, pyrrolidine $CH_2$), 2.49 (2H, m, C"2-$CH_2$), 2.23 (3H, s, pyrrolidine N—$CH_3$), 1.60-2.19 (5H, m, pyrrolidine $CH_2CH_2$), 1.30-1.55 (2H, m, C"3-$CH_2$).

Example 21

N,N'-Octane-1,8-diyl-bis-nicotinium Diiodide (bNOI)

S-(−)-Nicotine (30.8 mmol) was dissolved in glacial acetic acid (35 mL) and the solution was stirred at ambient temperature for 5 minutes. 1,8-Diiodooctane (15.4 mmol) was added to the solution and the mixture stirred and refluxed for 3 days. The mixture was then evaporated under reduced pressure to remove the solvent and the resulting oil was treated with an aqueous mixture of sodium bicarbonate. The aqueous mixture was extracted with ethyl ether (3×50 mL) and chloroform (3×50 mL) and the aqueous layer collected and was evaporated to dryness on a rotary evaporator, and the resulting solid was treated with chloroform and filtered. The filtrate was collected and evaporated to dryness. The resulting yellow oil was isolated in a 15% yield. $^1$H NMR (300 MHz, $CDCl_3$), δ 9.58 (1H, s, C2-H), 9.50 (1H, d, C6-H), 8.47 (1H, d, C4-H), 8.03 (1H, m. C3-H), 4.96 (2H, t, C"1-$CH_2$), 3.65 (1H, t, pyrrolidine $CH_2$), 3.24 (1H, t, pyrrolidine $CH_2$), 2.49 (2H, m, C"2-$CH_2$), 2.25 (3H, s, pyrrolidine N—$CH_3$), 1.60-2.19 (5H, m, pyrrolidine $CH_2CH_2$), 1.40-1.60 (4H, m, C"3&4-$CH_2$); $^{13}$C NMR (75 MHz, $CDCl_3$) δ 146.9, 143.8, 143.6, 143.5, 128.3, 66.8, 61.7, 57.0, 40.8, 36.1, 32.0, 27.7, 25.2, 23.5.

Example 22

N,N'-Nonane-1,9-diyl-bis-nicotinium Dibromide (bNNB)

S-(−)-Nicotine (30.8 mmol) was dissolved in glacial acetic acid (35 mL) and the solution was stirred at ambient temperature for 5 minutes. 1,9-Dibromononane (15.4 mmol) was added to the solution and the mixture stirred and refluxed for 3 days. The mixture was then evaporated under reduced pressure to remove the solvent and the resulting oil was treated with an aqueous mixture of sodium bicarbonate. The aqueous mixture was extracted with ethyl ether (3×50 mL) and chloroform (3×50 mL) and the aqueous layer collected and was evaporated to dryness on a rotary evaporator, and the resulting solid was treated with chloroform and filtered. The filtrate was collected and evaporated to dryness. The resulting yellow oil was isolated in a % yield. $^1$H NMR (300 MHz, $CDCl_3$), δ 9.75 (1H, s, C2-H), 9.56 (1H, d, C6-H), 8.49 (1H, d, C4-H), 8.08 (1H, m. C3-H), 5.05 (2H, t, C"1-$CH_2$), 3.65 (1H, t, pyrrolidine $CH_2$), 3.25 (1H, t, pyrrolidine $CH_2$), 2.48 (2H, m, C"2-$CH_2$), 2.25 (3H, s, pyrrolidine N—$CH_3$), 1.60-2.23 (5H, m, pyrrolidine $CH_2CH_2$), 1.30-1.60 (5H, m, C"3-5-$CH_2$).

Example 22

N,N'-Decane-1,10-diyl-bis-nicotinium Diiodide (bNDI)

S-(−)-Nicotine (30.8 mmol) was dissolved in glacial acetic acid (35 mL) and the solution was stirred at ambient temperature for 5 minutes. 1,10-Diiododecane (15.4 mmol) was added to the solution and the mixture stirred and refluxed for 3 days. The mixture was then evaporated under reduced pressure to remove the solvent and the resulting oil was treated with an aqueous mixture of sodium bicarbonate. The aqueous mixture was extracted with ethyl ether (3×50 mL) and chloroform (3×50 mL) and the aqueous layer collected and was evaporated to dryness on a rotary evaporator, and the resulting solid was treated with chloroform and filtered. The filtrate was collected and evaporated to dryness. The resulting yellow oil was isolated in a 27% yield. $^1$H NMR (300 MHz, $CDCl_3$) δ 9.55 (1H, s, C2-H), 9.44 (1H, d, C6-H), 8.53 (1H, d, C4-H), 8.09 (1H, m. C3-H), 4.98 (2H, t, C"1-$CH_2$), 3.74 (1H, t, pyrrolidine $CH_2$), 3.30 (1H, t, pyrrolidine $CH_2$, 2.50 (2H, m, C"2-$CH_2$), 2.29 (3H, s, pyrrolidine N—$CH_3$), 1.65-2.20 (5H, m, pyrrolidine $CH_2CH_2$), 1.30-1.57 (6H, m, C"3-5-$CH_2$); $^{13}$C NMR (75 MHz, CDCl$_3$) δ 146.6, 143.9×2, 143.4, 128.4, 66.9, 61.9, 57.0, 40.8, 36.1, 32.1, 28.5, 28.2, 25.8, 23.5.

Example 23

N,N'-Undecane-1,1'-diyl-bis-nicotinium Dibromide (bNUB)

S-(−)-Nicotine (30.8 mmol) was dissolved in glacial acetic acid (35 mL) and the solution was stirred at ambient temperature for 5 minutes. 1,11-Dibromoundecane (15.4 mmol) was added to the solution and the mixture stirred and refluxed for 3 days. The mixture was then evaporated under reduced pressure to remove the solvent and the resulting oil was treated with an aqueous mixture of sodium bicarbonate. The aqueous mixture was extracted with ethyl ether (3×50 mL) and chloroform (3×50 mL) and the aqueous layer collected and was evaporated to dryness on a rotary evaporator, and the resulting solid was treated with chloroform and filtered. The filtrate was collected and evaporated to dryness. The resulting yellow oil was isolated in a % yield. $^1$H NMR (300 MHz, CDCl$_3$) δ 9.70 (1H, s, C2-H), 9.47 (1H, d, C6-H), 8.49 (1H, d, C4-H), 8.12 (1H, m. C3-H), 5.02 (2H, t, C"1-CH$_2$), 3.65 (1H, t, pyrrolidine CH$_2$), 3.26 (1H, t, pyrrolidine CH$_2$), 2.49 (2H, m, C"2-CH$_2$), 2.25 (3H, s, pyrrolidine N—CH$_3$), 1.60-2.20 (5H, m, pyrrolidine CH$_2$CH$_2$), 1.20-1.50 (8H, m, C"3-6-CH$_2$); $^{13}$C NMR (75 MHz, CDCl$_3$) δ 146.5, 144.2, 143.7, 143.5, 128.4, 66.9, 61.9, 56.9, 40.7, 36.1, 32.2, 28.8, 28.7, 28.6, 25.9, 23.4.

Example 24

N,N'-Dodecane-1,12-diyl-bis-nicotinium Dibromide (bNDDB)

S-(−)-Nicotine (30.8 mmol) was dissolved in glacial acetic acid (35 mL) and the solution was stirred at ambient temperature for five minutes. 1,12-Dibromododecane (15.4 mmol) was added to the solution and the mixture stirred and refluxed for 3 days. The mixture was then evaporated under reduced pressure to remove the solvent and the resulting oil was treated with an aqueous mixture of sodium bicarbonate. The aqueous mixture was extracted with ethyl ether (3×50 mL) and chloroform (3×50 mL) and the aqueous layer collected and was evaporated to dryness on a rotary evaporator, and the resulting solid was treated with chloroform and filtered. The filtrate was collected and evaporated to dryness. The resulting yellow liquid was isolated in a 35% yield. $^1$H NMR (300 MHz, CDCl$_3$) δ 9.66 (1H, s, C2-H), 9.38 (1H, d, C6-H), 8.46 (1H, d, C4-H), 8.10 (1H, m. C3-H), 5.01 (2H, t, C"1-CH$_2$), 3.61 (1H, t, pyrrolidine CH$_2$), 3.25 (1H, t, pyrrolidine CH$_2$), 2.45 (2H, m, C"2-CH$_2$), 2.23 (3H, s, pyrrolidine N—CH$_3$), 1.60-2.19 (5H, m, pyrrolidine CH$_2$CH$_2$), 1.20-1.50 (8H, m, C"3-6-CH$_2$); $^{13}$C NMR (75 MHz, CDCl$_3$) δ 146.6, 144.2, 143.7, 143.4, 128.5, 67.0, 62.0, 60.0, 40.8, 36.1, 32.4, 29.0, 28.8, 28.7, 26.0, 23.5.

Example 25

N,N'-Hexame-1,6-diyl-bis-isoquinolinium Diiodide (bIQHxI)

1,6-Diiodohexane (mmol) was added to a solution (30 mL) of isoquinoline, and the solution heated for 24 hours at 65° C. The resulting precipitate was filtered, and the product washed five times with dry diethyl ether. The resulting yellow solid was isolated.

Example 26

N,N'-Octane-1,8-diyl-bis-isoquinolinium Diiodide (bIQOI)

1,8-Diiodooctane (mmol) was added to a solution (30 mL) of isoquinoline, and the solution heated for 24 hours at 65° C. The resulting precipitate was filtered, and the product washed five times with dry diethyl ether. The resulting yellow solid was isolated in an 92% yield. $^1$H NMR (300 MHz, DMSO-D$_6$) δ 10.05 (1H, d, C1-H), 8.77 (1H, d, C3-H), 8.58 (1H, d, C8-H), 8.48 (1H, d, C4-H), 8.35 (1H, d, C7-H), 8.26 (1H, t, C5-H), 8.07 (1H, t, C6-H), 4.68 (2H, t, C'1-CH$_2$), 2.00 (2H, m, C'2-CH$_2$), 1.30 (4H, m, C'3&4-CH$_2$).

Example 27

N,N'-Nonane-1,9-diyl-bis-isoquinolinium Dibromide (bIQNB)

1,9-Dibromononane (mmol) was added to a solution (30 mL) of isoquinoline, and the solution heated for 24 hours at 65° C. The resulting precipitate was filtered, and the product washed five times with dry diethyl ether. The resulting purple solid was isolated in a 92% yield. $^1$H NMR (300 MHz, DMSO-D$_6$) δ 10.17 (1H, d, C1-H), 8.85 (1H, d, C3-H), 8.62 (1H, d, C8-H), 8.49 (1H, d, C4-H), 8.36 (2H, d, C7-H), 8.26 (2H, t, C5-H), 8.08 (1H, t, C6-H), 4.72 (2H, t, C'1-CH$_2$), 2.02 (2H, m, C'2-CH$_2$), 1.78 (1H, m, C'3-CH$_2$), 1.19-1.50 (4H, m, C'3-5-CH$_2$).

Example 28

N,N'-Decane-1,10-diyl-bis-isoquinolinium Diiodide (bIQDI)

1,10-Diiododecane (mmol) was added to a solution (30 mL) of isoquinoline, and the solution heated for 24 hours at 65° C. The resulting precipitate was filtered, and the product washed five times with dry diethyl ether. The resulting yellow solid was isolated in a 92% yield. $^1$H NMR (300 MHz, DMSO-D$_6$) δ 10.07 (1H, d, C1-H), 8.78 (1H, d, C3-H), 8.58 (1H, d, C8-H), 8.48 (1H, d, C4-H), 8.36 (1H, d, C7-H), 8.26 (1H, t, C5-H), 8.07 (1H, t, C6-H), 4.69 (2H, t, C'1-CH$_2$), 2.0 (2H, m, C'2-CH$_2$), 1.15-1.50 (6H, m, C'3-5-CH$_2$).

Example 29

N,N'-Undecane-1,1'-diyl-bis-isoquinolinium Dibromide (bIQUB)

1,11-Dibromoundecane (mmol) was added to a solution (30 mL) of isoquinoline, and the solution heated for 24 hours at 65° C. The resulting precipitate was filtered, and the product washed five times with dry diethyl ether. The resulting off-white solid was isolated. $^1$H NMR (300 MHz, DMSO-D$_6$) δ 10.07 (1H, d, C1-H), 8.78 (1H, d, C3-H), 8.57 (1H, d, C8-H), 8.48 (1H, d, C4-H), 8.35 (1H, d, C7-H), 8.25 (1H, t, C5-H), 8.07 (1H, t, C6-H), 4.69 (2H, t, C'1-CH$_2$), 2.0 (2H, m, C'2-CH$_2$), 1.73 (1H, m, C'3-CH$_2$), 1.15-1.50 (6H, m, C'3-6-CH$_2$).

Example 30

N,N'-Dodecane-1,12-diyl-bis-isoquinolinium Dibromide (bIQDDB)

1,12-Dibromododecane (mmol) was added to a solution (30 mL) of isoquinoline, and the solution heated for 24 hours at 65° C. The resulting precipitate was filtered, and the product washed five times with dry diethyl ether. The resulting off-white solid was isolated. $^1$H NMR (300 MHz, DMSO-D$_6$) δ 10.06 (1H, d, C1-H), 8.78 (1H, d, C3-H), 8.58 (1H, d, C8-H), 8.48 (1H, d, C4-H), 8.35 (1H, d, C7-H), 8.25 (1H, t, C5-H), 8.07 (1H, t, C6-H), 4.70 (2H, t, C'1-CH$_2$), 2.0 (2H, m, C'2-CH$_2$), 1.75 (1H, m, C'3-CH$_2$), 1.15-1.40 (7H, m, C'3-6-CH$_2$).

Example 31

[$^3$H]Nicotine Binding Assay

Striata from two rats were dissected, pooled, and homogenized with a Tamar polytron in 10 volumes of ice-cold modified Krebs-HEPES buffer (20 mM HEPES, 118 mM NaCl, 4.8 mM KCl, 2.5 mM CaCl$_2$, 1.2 mM MgSO$_4$, adjusted to pH 7.5). The homogenates were incubated at 37° C. for five minutes and centrifuged at 15,000 g for 20 minutes. The pellet was resuspended in ten volumes of ice-cold MilliQ water, incubated for five minutes at 37° C., and centrifuged at 15,000 g for 20 minutes The second pellet was then resuspended in ten volumes of fresh ice-cold 10% Krebs-HEPES buffer, incubated at 37° C., and centrifuged at 15,000 g for 20 minutes. The latter sequence of resuspension, incubation, and centrifugation was repeated. The pellet was frozen under fresh 10% Krebs-HEPES buffer and stored at −40° C. until assay. Upon assay, the pellet was resuspended in the Krebs-HEPES buffer, incubated at 37° C. for five minutes, and centrifuged at 15,000 g for 20 minutes. The final pellet was resuspended in 3.6 ml ice-cold MilliQ water which provided for approximately 200 μg protein per 100 μl aliquot. Competition assays were performed in duplicate in a final volume of 200 μl Krebs-HEPES buffer containing 250 mmol Tris buffer (pH 7.5 at 4° C.). Reactions were initiated by addition of 100 μl of membrane suspension to 3 mM [$^3$H]nicotine (50 μl) and one of at least nine concentrations of analog (50 μl). After a 90 minute incubation at 4° C., reactions were terminated by dilution of the samples with 3 ml of ice-cold Krebs-HEPES buffer followed immediately by filtration through Whatman GF/B glass fiber filters (presoaked in 0.5% polyethyleneimine) using a Brandel Cell Harvester. Filters were rinsed three times with 3 ml of ice-cold Krebs-HEPES buffer, transferred to scintillation vials, and 5 ml scintillation cocktail (Research Products International Corp., Mt. Prospect, Ill.) added. Nonspecific binding determined in triplicate was defined as binding in the presence of 10 μM nicotine. Binding parameters were determined using the weighted, least squares non-linear regression.

The bis-alkyl pyridino analogs were evaluated for their ability to displace [$^3$H]nicotine binding from rat striatal membranes. The results are summarized in Table 1. Furthermore, the displacement by the analogs was compared to that produced by NONI, NDNI, and DHβE. All of the compounds examined displaced [$^3$H]nicotine binding with lower affinities than DHβE. However, bNDI had a value approaching the K$_i$ of DHβE and NDNI. Additionally, the N-alkyl-bis-pyridinium series demonstrated an increase in affinity for the receptor as the chain length of the carbon bridge increased.

TABLE 1

Specific Binding of [$^3$H]-Nicotine to Rat Striatal Nicotinic Acetylcholine Receptors in the Presence of bis-Alkyl Pyridino Analogs

| Compound | K$_i$ (μM)$^a$ |
|---|---|
| NONI | 49.3 |
| NDNI | 0.11 |
| DHβE | 0.15 |
| bPPeI | >100 |
| bPHxI | ND$^b$ |
| bPOI | 33.9 |
| bPNB | 24.1 |
| bPDI | 18.6 |
| bPUB | 14.4 |
| bPDDB | 9.14 |
| bPiHxI | ND |
| bPiOI | >100 |
| bPiNB | 66.7 |
| bPiDI | >100 |
| bPiUB | 82.0 |
| bPiDDB | 33.0 |
| bQHxI | ND |
| bQOI | >100 |
| bQNB | 20.1 |
| bQDI | >100 |
| bQUB | 38.3 (n = 2) |
| bQDDB | >100 |
| bIQHxI | ND |
| bIQOI | >100 |
| bIQNB | >100 |
| bIQDI | >100 |
| bIQUB | ND |
| bIQDDB | >100 |
| bNHxI | ND |
| bNOI | 1.50 |
| bNNB | 4.31 |
| bNDI | 0.28 |
| bNUB | 0.37 |
| bNDDB | 1.43 |

$^a$Data are expressed as fmol/mg of protein of at least 3 independent experiments. Specific binding is calculated as the difference between the total binding of 3 nM [$^3$H]-nicotine and nonspecific binding in the presence of 10 μM cold nicotine.
$^b$ND = Not Determined

Example 32

[$^3$H]MLA Binding Assay

Rat brain was dissected into the whole brain tissue without cortex, striatum and cerebellum and was frozen in liquid nitrogen and stored at −70° C. until use.

The brain tissue was homogenized with a Tekmar Polytron (setting 40) in 20 volumes of ice-cold hypotonic buffer (2 mM HEPES, 14.4 mM NaCl, 0.15 mM KCl, 0.2 mM CaCl$_2$ and 0.1 mM MgSO$_4$, pH=7.5). The homogenate was incubated at 37° C. for ten minutes and centrifuged at 25,000×g for 15 minutes at 40° C. The pellet was washed three times more by resuspension in the 20 volumes of the same buffer and centrifugation at the above parameters. The final pellet was stored at −20° C. under 4.6 ml of the incubation buffer and was suspended just before the incubation with radioligand.

The binding of [$^3$H]MLA to probe α7-type neuronal nicotinic acetylcholine receptors was measured using a modification of the method of Davies et al., "Characterisation of the binding of [$^3$H]methyllycaconitine: a new radioligand for labelling α7-type neuronal nicotinic acetylcholine receptors,' *Neuropharmocology*, 38, 679-690 (1999). [$^3$H]MLA (25.4 Ci/mmol) was purchased from Tocris Cookson Ltd., Bristol, U.K. Binding was performed in duplicate, in a final volume of 250 ml of the incubation medium, containing 20 mM HEPES, 144 mM NaCl, 1.5 mM KCl, 2 mM CaCl$_2$, 1 mM MgSO$_4$ and 0.05% BSA, pH=7.5. Reaction was initiated by the addition of 100 μl of membrane suspension to the samples containing a desired concentration of test compounds and 2.5 mM [$^3$H] MLA (final concentration) and incubated for 2 hours at room temperature. Total binding was measured in the absence of unlabelled ligand and nonspecific binding was determined in the presence of 1 µM unlabelled MLA. The binding reaction was terminated by dilution of samples with 3 ml of ice-cold incubation buffer followed by immediate filtration through presoaked in 0.5% polyethylenimine glass fiber filters (S&S, grade #32) using a Brandel harvester system. Filters were rinsed three times with 3 ml of ice-cold buffer, transferred to scintillation vials and 4 ml of scintillation cocktail was added. Protein was measured using the Bradford dye-binding procedure with bovine serum albumin as the standard.

In order to determine if these compounds have selectivity at the α7 receptor subtype, the bis-alkyl pyridino analogs were evaluated for their ability to displace [$^3$H]MLA binding from rat brain membranes, as a reflection of their interaction with the α7 receptor (Table 2). In addition, the classical α7 receptor antagonist α-bungarotoxin was also examined in this assay for comparison. α-Bungarotoxin afforded a $K_i$ value of 28.6±5.4 nM in this assay. The results from the competition binding assay showed that N,N'-dodecane-1,12-diyl-bis-pyridinium; Dibromide (bPDDB) and the N-alkyl-bis-quinolinium analogs demonstrated moderate binding affinity in the [$^3$H]MLA assay, while the other compounds showed no affinity no affinity for the α7 subtype.

TABLE 2

[$^3$H]MLA Binding in the Presence of bis-Alkyl Pyridino Analogs

| Compound | $K_i$ (µM)$^a$ |
|---|---|
| NONI | >100 |
| NDNI | >100 |
| DHβE | ND$^b$ |
| bPPeI | >100 |
| bPHxI | ND |
| bPOI | >100 |
| bPNB | >100 |
| bPDI | >100 |
| bPUB | 50.2 |
| bPDDB | 35.6 |
| bPiHxI | ND |
| bPiOI | >100 |
| bPiNB | >100 |
| bPiDI | >100 |
| bPiUB | >100 |
| bPiDDB | >100 |
| bQHxI | ND |
| bQOI | 2.01 |
| bQNB | 3.40 |
| bQDI | 7.32 |
| bQUB | 2.44 |
| bQDDB | 1.57 |
| bIQHxI | ND |
| bIQOI | 8.55 |
| bIQNB | 13.1 |
| bIQDI | 5.50 |
| bIQUB | 24.1 |
| bIQDDB | 12.3 |
| bNHxI | ND |
| bNOI | >100 |
| bNNB | >100 |
| bNDI | >100 |
| bNUB | >100 |
| bNDDB | >100 |

$^a$Data are expressed as fmol/mg of protein of 3 independent experiments. Specific binding is calculated as the difference between the total binding of 2.5 nM [$^3$H]-MLA to the receptors alone and its nonspecific binding in the presence of 1 µM cold MLA.
$^b$ND = Not Determined Example 33

[$^3$H]DA Release Assay

Rat striatal slices (500 µm thickness, 6-8 mg wet weight) were incubated for 30 minutes in Krebs buffer (118 mM NaCl, 4.7 mM KCl, 1.2 mM MgCl$_2$, 1.0 mM NaH$_2$PO$_4$, 1.3 mM CaCl$_2$, 11.1 mM glucose, 25 mM NaHCO$_3$, 0.11 mM L-ascorbic acid, and 0.004 mM disodium EDTA; pH 7.4, and saturated with 95% O$_2$/5% CO$_2$) in a metabolic shaker at 34° C. Slices were rinsed with 15 mL of fresh buffer and incubated for an additional 30 minutes in fresh buffer containing 0.1 µM [$^3$H]DA (6 slices/3 ml). Subsequently, slices were rinsed with 15 ml of fresh buffer and transferred to a glass superfusion chamber. Slices were superfused (1.0 ml/min) for 60 minutes with Krebs buffer containing nomifensine (10 µM) and pargyline (10 µM) and maintained at 34° C., pH 7.4, with continual aeration (95% O$_2$/5% CO$_2$). Two five minute samples (5 ml each) were collected to determine basal outflow of [$^3$H]DA. bis-Alkyl pyridino analogs were added to the superfusion buffer after the collection of the second sample and remained in the buffer until 12 consecutive five minute samples were collected. Subsequently, S-(−)-nicotine (10 µM) was added to the buffer and an additional 12 consecutive five minute samples were collected. At the end of the experiment, each slice was solubilized and the [$^3$H] content of the tissue determined.

Radioactivity in the superfusate and tissue samples was determined by liquid scintillation spectroscopy. Fractional release for tritium collected in each sample was divided by the total tritium present in the tissue at the time of sample collection and was expressed as a percentage of total tritium. Basal [$^3$H]outflow was calculated from the average of the tritium collected in the two five minute samples just before addition of the bis-alkyl pyridino analog. The sum of the increase in collected tritium resulting from either exposure to the test compound or exposure to S-(−)-nicotine in the absence and presence of the test compound equaled total [$^3$H]overflow. [$^3$H]Overflow was calculated by subtracting the [$^3$H]outflow during an equivalent period of prestimulation from the values in samples collected during and after drug exposure. Inasmuch as the radiolabelled compounds were not separated and identified, the tritium collected in superfusate is referred to as either [$^3$H]outflow or [$^3$H]overflow, rather than as [$^3$H]DA. [$^3$H]Overflow primarily represents [$^3$H]DA in the presence of nomifensine and pargyline in the superfusion buffer.

The bis-alkyl pyridino analogs were evaluated for their ability to evoke [$^3$H]DA release from rat striatal slices. In addition, the classical competitive nicotinic antagonist DHβE was also examined in this assay for comparison. None of the compounds examined had any significant [$^3$H]DA releasing properties in this assay in the concentration range tested. Since striatal nicotine-evoked [$^3$H]DA release is thought to be mediated through a mechanism involving the α3β2* receptor subtype, these compounds do not possess significant agonist activity at the α3β2* subtype.

The bis-alkyl pyridino analogs were also evaluated for their ability to inhibit nicotine-evoked [$^3$H]DA release. In these experiments, the striatal slices were superfused for 60 minutes with various concentrations of the analogs prior to nicotine (10 µM) exposure. Antagonist activity was evaluated by comparing the nicotine-evoked [$^3$H]overflow in the absence and presence of the analogs. The relative order of potency of the bis-alkyl pyridino analogs for inhibition of nicotine-evoked [$^3$H]DA release from rat striatal slices is illustrated in Table 3 by a comparison of their IC$_{50}$ values.

TABLE 3

Comparative IC$_{50}$s for bis-Alkyl Pyridino Analogs in the S-(−)-nicotine-evoked [$^3$H]DA Release Assay

| Compound | IC$_{50}$ (µM) |
|---|---|
| NONI | 0.62 |
| NDNI | >100 |
| DHβE | 1.0 |
| bPPeI | ND[b] |
| bPHxI | ND |
| bPOI | >1.0[a] |
| bPNB | ND |
| bPDI | >1.0[a] |
| bPUB | ND |
| bPDDB | 1.0 |
| bPHxI | ND |
| bPiOI | ND |
| bPiNB | ND |
| bPiDI | ND |
| bPiUB | ND |
| bPiDDB | 0.002 |
| bQHxI | ND |
| bQOI | ND |
| bQNB | ND |
| bQDI | ND |
| bQUB | ND |
| bQDDB | 0.020 |
| bIQHxI | ND |
| bIQOI | ND |
| bIQNB | ND |
| bIQDI | ND |
| bIQUB | ND |
| bIQDDB | ND |
| bNHxI | ND |
| bNOI | ND |
| bNNB | ND |
| bNDI | ND |
| bNUB | ND |
| bNDDB | 4.37 |

[a] Compounds only tested for two concentration points 0.1 and 1.0 µM
[b] ND = Not Determined

Example 34

Compounds 1-3 (FIG. 3) were prepared by reacting S-(−)-nicotine with the appropriate n-alkyl iodide in glacial acetic acid, utilizing the procedure described by Crooks, et al., *Drug Dev. Res.* 1995, 36, 91-102. The N-n-alkylpyridinium salts 4-7 (FIG. 3) were obtained via n-alkylation of pyridine with the appropriate n-alkyl halide. The conformationally restricted racemic syn- and anti-nicotine analogs 8-12 and 13-17, respectively (FIG. 3), were prepared via regiospecific alkylation of the pyridine-N atom of the corresponding free base. The syn-free base was synthesized from 7-aza-1-tetralone, and the anti-free base was prepared from 5-aza-1-tetralone. N,N'-Dodecanediyl-bis-nicotinium dibromide, 18 (FIG. 4), was prepared by dissolving S-(−)-nicotine in glacial acetic acid, stirring the mixture for five minutes and then adding dibromododecane. The solution was stirred under reflux for three days, the solvent was evaporated under reduced pressure, and the resulting residue was treated with an aqueous saturated solution of NaHCO$_3$. The resulting mixture was then extracted with diethyl ether (3×50 mL), and then with chloroform (3×50 mL). The aqueous layer was collected and lyophilized for 24 hours, and the resulting solid was triturated with chloroform. After filtration, the filtrate was dried over anhydrous MgSO$_4$ and removal of solvent afforded the bis-nicotinium salt, 18. N,N'-Dodecanediyl-bis-pyridinium dibromide, 19 (FIG. 4) was prepared by reacting an excess of pyridine with dibromododecane for 24 hours at 65° C. in the absence of solvent. The resulting solid was collected by filtration, dissolved in water, and the aqueous solution washed with diethyl ether (3×50 mL). The aqueous solution was then lyophilized to afford 19 as a crystalline solid.

All compounds were characterized by $^1$H and $^{13}$C NMR spectroscopy, mass spectroscopy and elemental analysis.

Biological Assays

Subjects.

Male Sprague-Dawley rats (225-250 g) were obtained from Harlan Industries (Indianapolis, Ind.) and housed two per cage with free access to food and water in the Division of Lab Animal Resources in the College of Pharmacy at the University of Kentucky. All experiments were carried out in accordance with the 1996 NIH Guide for the Care and Use of Laboratory Animals and were approved by the Institutional Animal Care and Use Committee at the University of Kentucky.

[$^3$H]-Dopamine Overflow from Superfused Striatal Slices.

[$^3$H]-Dopamine release assays were performed according to Dwoskin, L. P., and Zahniser, N. R., *J. Pharmacol. Exp. Ther.* 1986, 239, 442; Miller, D. K., et al., *J. Pharmacol. Exp. Ther.* 2002, 302, 1113; Reuben, M., Clarke, P. B., *Neuropharmacology* 2000, 39, 290, with minor modifications. Striatal coronal slices (500 µm, 4-6 mg) were obtained and incubated for 30 minutes in Krebs' buffer (in mM: 118 NaCl, 4.7 KCl, 1.2 MgCl$_2$, 1 NaH$_2$PO$_4$, 1.3 CaCl$_2$, 11.1 glucose, 25 NaHCO$_3$, 0.11 L-ascorbic acid and 0.004 disodium EDTA, pH 7.4, saturated with 95% O$_2$/5% CO$_2$) in a metabolic shaker at 34° C. Slices were incubated with 0.1 µM (final concentration) of [$^3$H]-dopamine during the latter 30 minutes of the 60-minute incubation period. Each slice was transferred to a glass superfusion chamber maintained at 34° C. and superfused (1 ml/min) with Krebs' buffer containing nomifensine (10 µM) and pargyline (10 µM) to inhibit [$^3$H]-dopamine reuptake after release into the extracellular space, ensuring that [$^3$H]-overflow primarily represented [$^3$H]-dopamine. Sample collection (5-minute; 5 mL) began after 60 minutes of superfusion. The ability of N-n-alkylated nicotinium, N-n-alkylated pyridinium, conformationally restricted N-n-alkylated nicotinium and bis-azaaromatic quaternary ammonium analogs to evoke [$^3$H]-dopamine release (intrinsic activity) and to inhibit nicotine-evoked [$^3$H]-dopamine release (act as antagonists) were determined. At the end of the experiment, each slice was solubilized, and the [$^3$H]-content of the tissue determined. Release during each minute was normalized for total tissue [$^3$H]-content. Analog-induced intrinsic activity and inhibitory activity were determined using slices from the same rat (repeated-measures design).

The amount of [$^3$H] in each sample was calculated by dividing the total [$^3$H] collected in each sample by the total in the tissue at the time of sample collection (defined as fractional release). The sum of all the increases in [$^3$H]-dopamine fractional release resulting from either exposure to analog or nicotine equaled "total overflow". "Overflow," rather than "release," is the more correct terminology because the neurotransmitter measured is the net result of release and reuptake. Data were analyzed by weighted, least squares regression analysis of the sigmoidal concentration-effect curves to obtain EC$_{50}$ and IC$_{50}$ values.

[$^3$H]-Nicotine (α4β2* Subtype) and [$^3$H]-Methyllycaconitine (α7* Subtype) Binding Assays.

Whole brain, excluding cortex and cerebellum, was homogenized in 20 ml of ice-cold buffer, containing (in mM): 2 HEPES, 11.8 NaCl, 0.48 KCl, 0.25 CaCl$_2$ and 0.12 MgSO$_4$, pH 7.5. Homogenate was centrifuged (25,000 g, 15 minutes, 4° C.). Pellets were resuspended in 20 ml of buffer and incubated at 37° C., for ten minutes, cooled to 4° C. and centrifuged (25,000 g, 15 minutes, 4° C.). Pellets were resuspended and centrifuged using the same conditions. Final pellets were stored in assay buffer, containing (in mM): 20 HEPES, 118 NaCl, 4.8 KCl, 2.5 CaCl$_2$, and 1.2 MgSO$_4$) pH 7.5 at −70° C. Upon use, final pellets were resuspended in ~20 ml assay buffer. Samples (250 µl) contained 100-140 µg of membrane protein, 3 nM [$^3$H]-nicotine or 3 nM [$^3$H]-methyllycaconitine, and analog (0.1 µM-1 mM) in assay buffer containing 50 mM Tris. Control was in the absence of analog. In [$^3$H]-nicotine and [$^3$H]-methyllycaconitine binding assays, nonspecific binding was determined in the presence of 10 µM nicotine, and 10 µM methyllycaconitine, respectively. Incubations proceeded for 60 minutes at room temperature using 96-well plates and were terminated by harvesting on Unifilter-96 GF/B filter plates presoaked in 0.5% polyethylenimine, using a Packard FilterMate harvester.

After washing five times with 350 µl ice-cold assay buffer, filter plates were dried (60 minutes, 49° C.), bottom-sealed, and filled with Packard's MicroScint 20 cocktail (40 µl/well). After 60 minutes, filter plates were top-sealed, and radioactivity determined using a Packard TopCount. Protein concentrations were determined using bovine serum albumin as the standard.

Blood-Brain Barrier Choline Transporter Affinity Assays.

Quaternary ammonium analogs were evaluated for their ability to inhibit [$^3$H]-choline uptake into brain providing an indication of the ability of these analogs to interact with the choline transporter. These assays were conducted using the in situ rat brain perfusion method of Takasato, et al., *Am. J. Physiol.* 1984, 247, 484, as modified by Allen and Smith, *J. Neurochem.*, 2001, 76, 1032. Inhibition coefficients (K$_i$, concentration of analog inhibiting 50% of [$^3$H]-choline uptake into brain) were determined using a single inhibitor concentration as described by Smith, et al., *J. Neurochem.*, 1987, 49, 1651. K$_i$ values were compared by ANOVA followed by Bonferoni's multiple comparisons test to determine if an analog inhibits [$^3$H]-choline uptake.

TABLE 4

Evaluation of N-n-alkylnicotinium analogs at native nAChRs.

| Compound | Nicotine-evoked [$^3$H]DA Overflow IC$_{50}$ µM[a] | [$^3$H]Nicotine Binding K$_i$ µM[b] | [$^3$H]MLA Binding K$_i$ µM[b] |
|---|---|---|---|
| NONI | 0.62 (0.20-1.9) | 20 (15-25) | 12 (9.2-16) |
| NDNI | na | 0.09 (0.08-0.11) | na |
| NDDNI | 0.009 (0.003-0.03) | 0.14 (0.11-0.17) | na |

[a]Values are means of three to ten independent experiments, 95% confidence interval is given in parentheses (na = not active).
[b]Values are means of four to ten independent experiments, 95% confidence interval is given in parentheses (na = not active).

Example 35

Simple N-n-alkylpyridiniums, with alkyl chain lengths ranging from C$_1$ to C$_{20}$, exhibit moderate to low affinity for nAChR subtypes mediating nicotine-evoked DA release and for α4β2* nAChRs (IC$_{50}$=90-530 nM and Ki=9-44 µM, respectively; Table 5). These compounds also lack affinity for α7* nAChRs. These data demonstrate the importance of the 3-(2'-pyrrolidino) moiety in the N-n-alkylnicotinium series of compounds for potent inhibition of nAChR subtypes mediating nicotine-evoked dopamine release.

TABLE 5

Inhibitory activity of simple N-n-alkylpyridinium analogs at native nAChRs.

| Compound | Nicotine-evoked [$^3$H]DA Overflow IC$_{50}$ µM[a] | [$^3$H]Nicotine Binding K$_i$ µM[b] | [$^3$H]MLA Binding K$_i$ µM[b] |
|---|---|---|---|
| NDPI | 0.13 (0.02-0.87) | 17 (14-20) | na |
| NDDPI | 0.26 (0.02-4.23) | na | na |
| NPDPB | 0.32 (0.11-0.87) | 38 (28-51) | na |
| NEcPB | 0.12 (0.01-2.38) | na | na |

[a]Values are means of five to six independent experiments, 95% confidence interval is given in parentheses.
[b]Values are means of four independent experiments, 95% confidence interval is given in parentheses (na = not active.)

Example 36

The nAChR receptor properties of some conformationally restricted analogs of the above N-n-alkylnicotinium compounds are shown in Table 6. These analogs were designed to assess the rotameric preference about the C3-C2' bond of NONI and NDNI for interaction with nAChR subtypes. Two classes of bridged nicotinium analogs, representing extreme rotameric conformations (i.e. syn- and anti-rotamers, FIG. 3) were examined. Interestingly, these conformationally restrained analogs lacked affinity for α4β2* and α7* nAChRs, as determined from [$^3$H]-nicotine and [$^3$H]-methyllycaconitine binding assays. In addition, with the exception of BCDD, these analogs potently and selectively inhibited nicotine-evoked [$^3$H]-dopamine release (IC$_{50}$ values 30-660 nM), although no clearly defined structure-activity trends could be determined. These analogs may be interacting with multiple nAChR subtypes mediating nicotine-evoked dopamine release. Alternatively the lack of structure-activity relationships within this group may be due to the fact that these molecules are racemic in nature. It is conceivable that the optical isomers of each compound may exhibit different affinities at the nAChR subtypes examined, thus confounding the structural analysis.

TABLE 6

Inhibitory activity of simple N-n-alkylpyridinium analogs at native nAChRs

| Compound | Nicotine-evoked [$^3$H]DA Overflow IC$_{50}$ µM[a] | [$^3$H]Nicotine Binding[b] | [$^3$H]MLA Binding[b] |
|---|---|---|---|
| ACO | 0.08 (±0.04) | na | na |
| ACN | 0.66 (±0.03) | na | na |
| ACD | 0.58 (±0.55) | na | na |
| ACU | 0.04 (±0.02) | na | na |
| ACDD | 0.22 (±0.15) | na | na |
| BCO | 0.04 (±0.02) | na | na |
| BCN | 0.31 (±0.01) | na | na |
| BCD | 0.03 (±0.03) | na | na |
| BCU | 0.04 (±0.03) | na | na |
| BCDD | na | na | na |

[a]Values are means of six to eight independent experiments for the DA release assay, standard error is given in parentheses (na = not active).
[b]Determined at a single 10 µM concentration in four independent experiments.

Example 37

The bis-azaaromatic quaternary ammonium analogs: N,N'-dodecanediyl-bis-nicotinium dibromide (18, FIG. 4), and N,N'-dodecanediyl-bis-pyridinium dibromide (19, FIG. 4), were synthesized and evaluated for their inhibitory properties at nAChR subtypes (Table 7). $C_{12}$ analogs were studied, based on our findings that the $C_{12}$ analog (NDDNI) in the N-n-alkylnicotinium series was the most potent as an inhibitor of the nAChR subtype mediating nicotine-evoked [$^3$H]-dopamine overflow. These compounds were not potent or selective for the subtype mediating nicotine-evoked dopamine release.

TABLE 7

Inhibitory activity of N,N'-bis-azaaromatic quaternary ammonium $C_{12}$ analogs, bNDDB and bPDDB, at native nAChRs.

| Compound | Nicotine-evoked [$^3$H]DA Overflow IC$_{50}$ μM$^a$ | [$^3$H]Nicotine Binding K$_i$ μM$^b$ | [$^3$H]MLA Binding K$_i$ μM$^b$ |
|---|---|---|---|
| bNDDB | 0.17 (±0.13) | 1.95 (±0.19) | na |
| bPDDB | 1.00 (±0.38) | 9.15 (±0.17) | 33 (±4.6) |

$^a$Values are means of four to six experiments, standard error is given in parentheses.
$^b$Values are means of three to four experiments, standard error is given in parentheses (na = not active).

Example 38

Analog Affinity for, and Transport by, the Blood-Brain Barrier Choline Transporter Several N-n-alkylnicotinium analogs have been shown to have good affinity for the blood-brain barrier choline transporter. Specifically, NONI, inhibits [$^3$H]-choline uptake (Table 8) with an apparent K$_i$ value of 49 μM (±24 μM). The $C_1$ analog, NMNI, shows low affinity for the transporter, with an apparent K$_i$ value of greater than 1000 μM. The $C_{10}$ analog, NDNI, inhibits [$^3$H]-choline uptake into brain with an apparent K$_i$ value of 27 μM (±2 μM), similar to NONI and choline. The $C_4$ analog, NBNI, has an apparent K$_i$ value of 777±588 μM. These results demonstrate that increasing the length of the N-n-alkyl chain in these N-n-alkylnicotinium analogs facilitates transporter binding, and thus, enhances brain uptake via the blood-brain barrier choline transporter.

TABLE 8

Affinity of N-n-alkylcholine analogs and N-n-alkylnicotinium analogs for the blood brain barrier choline transporter.

| Compound | Concentration μM$^a$ | Ki μM$^a$ |
|---|---|---|
| N-n-Octylcholine | 10 | 1.7 (±0.3) |
| N-n-Hexylcholine | 10 | 2.2 (±0.1) |
| N-n-Octylpyridinium iodide | 250 | 32 (±22) |
| NBNI | 250 | 777 (±590) |
| NONI | 250 | 49 (±24) |
| NDNI | 250 | 27 (±0.1) |

$^a$Values are means of three to five independent experiments, standard error is given in parentheses.
$^b$In vitro therapeutic index (IC$_{50}$ cytotoxicity/IC$_{50}$ complement inhibition)

Example 39

[$^3$H]-NONI Brain Uptake

Considering the above K$_i$ value for NONI, experiments were performed to verify that this compound gains access to brain via the blood-brain barrier choline transporter. Thus, brain distribution parameters of [$^3$H]-NONI were determined. Uptake of [$^3$H]-NONI (1 μCi/ml) into rat brain was evaluated from 0-60 seconds in the absence of unlabeled NONI. The transfer coefficient value (K$_{in}$) for [$^3$H]-NONI uptake was 1.59±0.14×10$^{-3}$ ml/s/g, calculated from the slope of the compound accumulating in brain versus time. An uptake time of 45 seconds was chosen as within the linear portion of the brain uptake curve in order to evaluate [$^3$H]-NONI brain uptake in the presence of unlabeled NONI. Unlabeled NONI (250 μM) in the perfusion fluid resulted in 46% inhibition of [$^3$H]-NONI brain uptake, suggesting saturable kinetic parameters associated with NONI transport into brain.

The ability of choline to inhibit [$^3$H]-NONI uptake into brain and [$^3$H]-NONI distribution parameters were also determined. The permeability-surface area product (PA; ml/s/g) for [$^3$H]-NONI with no inhibitors present was 1.64±0.37× 10$^{-3}$ ml/s/g, determined as a single time point PA value. If NONI is transported in total, or in part, by the blood-brain barrier choline transporter, then addition of choline to the perfusion fluid should reduce brain uptake of [$^3$H]-NONI. When 500 μM choline was added to the perfusion fluid the PA for [$^3$H]-NONI decreased ~25% to 1.24±0.5×10$^{-3}$ ml/s/g. A higher concentration (5 mM) of choline further reduced the uptake of [$^3$H]-NONI to 7.55±3.30×10$^4$ ml/s/g, which was <50% of the uptake in the absence of choline. These results demonstrate that a significant component of NONI uptake occurs via the blood-brain barrier choline transporter.

Example 40

Figure 5:
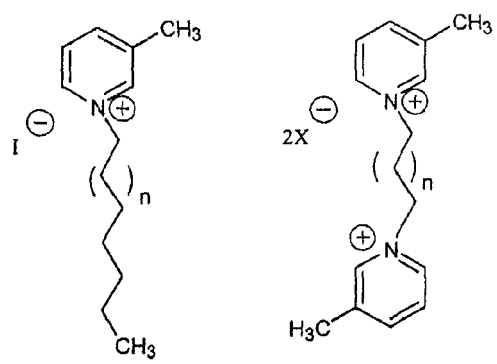
FIG. 5 shows the chemical structures of the analogs of N-n-alkylpicolinium (on the left) and N,N'-alkyl-bis-picolinium (on the right).

N-n-Alkylpicolinium analogs shown in FIG. 5 were prepared by reacting 3-picoline with the appropriate n-alkyl iodide utilizing conditions described in Crooks, et al., *Drug Dev. Res.* 1995, 36, 91. The N,N'-alkyl-bis-picolinium analogs shown in FIG. 5 were prepared by reacting an excess of 3-picoline with a variety of diiodo- or dibromoalkanes for 24 hours in the absence of solvent. The resulting solid was collected by filtration, dissolved in water and the aqueous solution was washed with diethyl ether (3×50 mL). The aqueous solution was then lyophilized to afford either a solid or viscous hygroscopic oil. All compounds were characterized by $^1$H and $^{13}$C NMR spectroscopy, mass spectroscopy and elemental analysis.

Biological Assays:

Male Sprague-Dawley rats (225-250 g) were obtained from Harlan Industries (Indianapolis, Ind.) and housed two per cage with free access to food and water in the Division of Lab Animal Resources in the College of Pharmacy at the University of Kentucky. All experiments were carried out in accordance with the 1996 NIH Guide for the Care and Use of Laboratory Animals and were approved by the Institutional Animal Care and Use Committee at the University of Kentucky.

[$^3$H]DA release assays were performed according to previously published methods with minor modifications. Striatal slices (500 μm, 4-6 mg) were incubated for 30 minutes in Krebs' buffer (in mM: 118 NaCl, 4.7 KCl, 1.2 MgCl$_2$, 1 NaH$_2$PO$_4$, 1.3 CaCl$_2$, 11.1 glucose, 25 NaHCO$_3$, 0.11 L-ascorbic acid and 0.004 disodium EDTA, pH 7.4, saturated with 95% O$_2$/5% CO$_2$) in a metabolic shaker at 34° C. Slices were incubated with 0.1 μM (final concentration) [$^3$H]DA during the latter 30 minutes of the 60-minute incubation period. Each slice was transferred to a glass superfusion chamber maintained at 34° C. and superfused (1 ml/min) with Krebs' buffer containing nomifensine (10 μM) and pargyline (10 μM) to inhibit [$^3$H]DA reuptake and metabolism, respectively, after release into the extracellular space, ensuring that [$^3$H]overflow primarily represents [$^3$H]DA. Sample collection (5-minute; 5 ml) began after 60 minutes of superfusion. The ability of N-n-alkylpicolinium and N,N'-alkyl-bis-picolinium analogs to evoke [$^3$H]DA release (i.e., exhibit intrinsic activity) and to inhibit nicotine-evoked [$^3$H]DA release (i.e., act as nAChR antagonists) were determined. To establish that these analogs act as nAChR antagonists, by definition, inhibition of the response to nicotine must be observed at analog concentrations that do not evoke a response. Thus, the ability of these analogs to elicit intrinsic activity (evoke [$^3$H] DA overflow) was determined. At the end of the experiment, each slice was solubilized and [$^3$H]content of the tissue determined. Release during each minute was normalized for total [$^3$H]content of the slice. Analog-induced intrinsic activity and inhibitory activity were determined using slices from the same rat (repeated-measures design).

Fractional release was calculated by dividing the total tritium collected in each sample by the total tritium in the tissue at the time of sample collection. The sum of all the increases in [$^3$H]DA fractional release resulting from either exposure to analog or nicotine equaled "total [H]DA overflow". "Overflow," rather than "release," is the more correct terminology because the neurotransmitter measured is the net result of release and reuptake. Typically, data were analyzed by weighted, least squares regression analysis of sigmoidal concentration-effect curves to obtain $EC_{50}$ and $IC_{50}$ values.

Interaction of the analogs with nAChR subtypes probed by [$^3$H]nicotine binding ($\alpha4\beta2$*) and [$^3$H]MLA binding ($\alpha7$*) to rat brain membranes was determined to assess nAChR subtype selectivity of the analogs. [$^3$H]Nicotine and [$^3$H] MLA binding assays were performed using whole brain, excluding cortex and cerebellum. Whole brain was homogenized in 20 ml of ice-cold buffer (in mM: 2 HEPES, 11.8 NaCl, 0.48 KCl, 0.25 $CaCl_2$, and 0.12 $MgSO_4$, pH 7.5). Homogenates were centrifuged (25,000 g, 15 minutes, 4° C.). Pellets were resuspended in 20 ml of buffer and incubated at 37° C., for 10 minutes, cooled to 4° C. and centrifuged (25,000 g, 15 minutes, 4° C.). Pellets were resuspended and centrifuged again using the same conditions. Final pellets were stored at −70° C. in assay buffer (in mM: 20 HEPES, 118 NaCl, 4.8 KCl, 2.5 $CaCl_2$, and 1.2 $MgSO_4$, pH 7.5). Upon use, final pellets were resuspended in ~20 ml assay buffer. Samples (250 µl) contained 100-140 µg of membrane protein, 3 nM [$^3$H]nicotine or 3 nM [$^3$H]MLA, and a range of concentrations (0.1 µM-1 mM) of analog in assay buffer containing 50 mM Tris. Control was in the absence of analog. In [$^3$H]nicotine and [$^3$H]MLA binding assays, nonspecific binding was determined in the presence of 10 µM nicotine and 10 µM MLA, respectively. Incubation proceeded for 60 minutes at room temperature using 96-well plates and was terminated by harvesting on Unifilter-96 GF/B filter plates, presoaked in 0.5% polyethylenimine, using a Packard FiterMate harvester. After washing 5× with 350 µl ice-cold assay buffer, filter plates were dried (60 minutes, 49° C.), bottom-sealed, and filled with Packard's MicroScint 20 cocktail (40 µl/well). After 60 minutes, filter plates were top-sealed, and radioactivity determined. Protein concentration was determined using BSA as the standard. The results are shown in Table 9.

TABLE 9

Inhibitory activity of N-n-alkylpicolinium iodide analogs at native nAChRs.

| Compound | Nicotine-evoked [$^3$H]DA Overflow $IC_{50}$ µM$^a$ | [$^3$H]Nicotine Binding $K_i$ µM$^b$ | [$^3$H]MLA Binding $K_i$ µM$^b$ |
|---|---|---|---|
| NOPiI | 1.0 (±0.09) | Na | Na |
| NNPiI | nd | 62 (±17) | Na |
| NDPiI | 0.3 (±0.05) | 26 (±3.6) | Na |
| NUPiI | nd | Na | Na |
| NDDPiI | 0.03 (±0.02) | Na | Na |

$^a$Values are means of three to five independent experiments, standard error is given in parenthesis (nd = not determined).
$^b$Values are means of four independent experiments, standard error is given in parentheses (na = not active).

Table 9 shows the inhibitory activity of the N-n-alkylpicolinium analogs with carbon chain lengths of $C_8$-$C_{12}$ in the nicotine-evoked [$^3$H]DA overflow assay and in the [$^3$H]nicotine and [$^3$H]MLA binding assays. This series of analogs was relatively selective for the nAChR subtype(s) mediating nicotine-evoked [$^3$H]DA overflow, in that, these analogs did not inhibit binding of either [$^3$H]nicotine and [$^3$H]MLA to rat brain membranes, indicating low affinity for or no interaction with $\alpha4\beta2$* and $\alpha7$* nAChRs.

In the nicotine-evoked [$^3$H]DA overflow assay, NDDPiI at concentrations of ≥1.0 µM evoked [$^3$H]DA overflow, and thus, exhibited intrinsic activity; whereas the $C_8$ and $C_{10}$ analogs demonstrated no intrinsic activity up to 1.0 µM. As the carbon chain length was increased the inhibitory potency at nAChRs mediating nicotine-evoked [$^3$H]DA overflow increased with a rank order of NDDPiI>NDPiI>NOPiI (Table 9). The most potent analog in the series was NDDPiI ($IC_{50}$=30 nM). Furthermore, NDDPiI inhibited nicotine-evoked [$^3$H]DA overflow by 63%, indicating that this analog may interact with a single subtype of nAChR that mediates this effect of nicotine.

Table 10 illustrates the ability of a series of N,N'-bis-alkylpicolinium analogs with carbon chain lengths of $C_6$-$C_{12}$ to inhibit nicotine-evoked [$^3$H]DA overflow and the binding of [$^3$H]nicotine and [$^3$H]MLA to rat brain membranes. None of the analogs in this series inhibited either [$^3$H]nicotine or [$^3$H]MLA binding with high affinity, indicating no affinity at $\alpha7$,* nAChRs and only low affinity at $\alpha4\beta2$* nAChRs.

Furthermore, none of the N,N'-bis-alkylpicolinium analogs in this series evoked [$^3$H]DA overflow, and thus, they did not exhibit intrinsic activity at subtypes mediating nicotine-evoked DA release. The most active analogs in this series are those with the longer n-alkyl chain length and with an even number of carbon atoms (Table 10). bPiDDB (the $C_{12}$ analog) was the most potent ($IC_{50}$=5 nM) inhibitor of the nAChR subtype mediating nicotine-evoked [$^3$H]DA overflow. bPiDDB is also selective for the nAChR subtype mediating nicotine-evoked [$^3$H]DA overflow, since it has low or no affinity for the $\alpha4\beta2$* and $\alpha7$* nAChR subtypes (Table 10). Thus, bPiDDB is a selective inhibitor of the nAChR subtype that mediates nicotine-evoked [$^3$H]DA overflow. bPiDDB is approximately 320-fold more potent than DHβE in inhibiting nicotine-evoked [$^3$H]DA overflow. bPiDDB and the other analogs in this series inhibited [$^3$H]DA overflow by a maximum of 60%, similar to the maximum inhibition observed for conotoxin-MII, suggesting that this small synthetic molecule (bPiDDB) and the neurotoxic Conus peptide of higher molecular weight may be acting at the same nAChR subtype to inhibit nicotine-evoked DA release.

TABLE 10

Inhibitory activity of N,N'-bis-picolinium salts at native nAChRs.

| Compound | Nicotine-evoked [³H]DA Overflow IC$_{50}$ µM[a] | [³H]Nicotine Binding K$_i$ µM[b] | [³H]MLA Binding K$_i$ µM[b] |
|---|---|---|---|
| bPiHxI  | 1.66 (±0.85)   | Na       | Na |
| bPiOI   | 0.01 (±0.009)  | Na       | Na |
| bPiNB   | 1.52 (±0.34)   | 80 (±17) | Na |
| bPiDI   | 0.03 (±0.01)   | Na       | Na |
| bPiUB   | 1.61 (±1.08)   | 69 (±29) | Na |
| bPiDDB  | 0.005 (±0.003) | 49 (±17) | Na |

[a]Values are means of four to six independent experiments, standard error is given in parenthesis.
[b]Values are means of four independent experiments, standard error is given in parentheses (na = not active).

The N,N'-dodecyl-bis-azaaromatic analogs (i.e. the C$_{12}$ analogs) were tested and compared for their inhibitory activity. The compounds tested included the dibromide salts of the C$_{12}$ analogs of bis-nicotinium (bNDDB), bis-pyridinium (bPDDB), bis-picolinium (bPiDDB), bis-quinolinium (bQDDB), and bis-isoquinolinium (bIQDDB). The results are shown in Table 11.

TABLE 11

Inhibitory activity of the C$_{12}$ N,N'-bis-Azaaromatic analogs.

| Compound | Nicotine-evoked [³H]DA Overflow IC$_{50}$ (µM) | [³H]DA Uptake K$_i$ (µM) | [³H]Nicotine Binding K$_i$ (µM) | [³H]MLA Binding K$_i$ (µM) |
|---|---|---|---|---|
| bNDDB  | 0.04 ± 0.02    | 43.2 ± 14.9 | 1.95 ± 0.19 | >100        |
| bPDDB  | 1.00 ± 0.38    | >100        | 9.15 ± 0.17 | 33 ± 4.6    |
| bPiDDB | 0.005 ± 0.003  | >100        | 48.6 ± 17.2 | >100        |
| bQDDB  | 0.021 ± 0.01   | 3.86 ± 0.22 | >100        | 1.61 ± 0.21 |
| bIQDDB | 0.007 ± 0.003  | 0.27 ± 0.07 | 6.10 ± 0.73 | 2.21 ± 0.25 | bPiDDB has 4-5 orders of magnitude higher affinity for the nAChR subtype mediating nicotine-evoked [³H]DA overflow compared to its affinity at both α4β2* and α7* nAChRs. Thus, based on the preclinical data, by inhibiting dopamine release bPiDDB and related analogs should diminish the rewarding effects produced by nicotine self-administration and serve as tobacco use cessation agents.

What is claimed is:

1. A method of treating a dopamine mediated disease state comprising administering to an individual in need thereof an effective amount of a composition comprising at least one nicotine antagonist having the formula

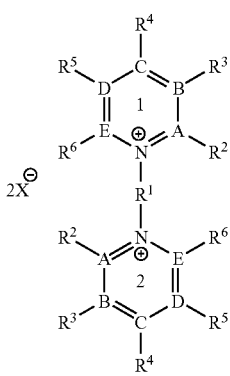

V wherein:
  Rings 1 and 2 are pyridinium;
  $R^2$, $R^3$, $R^4$, $R^5$, $R^6$ are each independently selected from hydrogen; alkyl; and substituted alkyl;
  $R^1$ is selected from alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, heterocyclic, substituted heterocyclic, alkoxy, alkylamine, thioalkyl; and
  X is selected from Cl, Br, I, HSO$_4$, ½SO$_2$, CH$_3$SO$_3$, p-TsO, CF$_3$SO$_3$ and any ion that completes the salt form of the nicotine antagonist; and enantomers, diastereomers and racemic mixes thereof,
wherein the nicotine antagonist binds to nAChR and inhibits release of dopamine.

2. The method of claim 1 wherein the dopamine mediated disease state is selected from the group consisting of myasthenia gravis, Parkinson's disease, Alzheimer's disease, schizophrenia, eating disorders, and drug addiction.

3. The method of claim 2 wherein said drug addiction is to a drug selected from the group consisting of nicotinic agonists, cocaine, amphetamines, caffeine, phencyclidine, opiates, barbituates, benzodiazepines, cannabinoids, hallucinogens and alcohol.

4. The method of claim 2 wherein the composition is administered orally, transdermally, transnasally, rectally, sublinguinally, subdermally, intraocularly or via smokeless inhalation.

5. A method of treating drug addiction in a patient comprising administering to the patient an effective amount of a composition comprising at least one nicotine antagonist having the formula

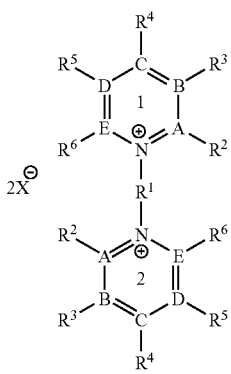

V wherein:
  Rings 1 and 2 are pyridinium;
  $R^2$, $R^3$, $R^4$, $R^5$, $R^6$ are each independently selected from hydrogen; alkyl and substituted alkyl;
  $R^1$ is selected from alkyl, substituted alkyl, cycloalkyl, substituted cycloalkyl, alkenyl, substituted alkenyl, alkynyl, substituted alkynyl, aryl, substituted aryl, arylalkyl, substituted arylalkyl, arylalkenyl, substituted arylalkenyl, arylalkynyl, substituted arylalkynyl, heterocyclic, substituted heterocyclic, alkoxy, alkylamine, thioalkyl; and
  X is selected from Cl, Br, I, HSO$_4$, ½SO$_2$, CH$_3$SO$_3$, p-TsO, CF$_3$SO$_3$ and any ion that completes the salt form of the nicotine antagonist; and enantomers, diastereomers and racemic mixes thereof, wherein the nicotine antagonist binds to nAChR and inhibits the release of dopamine.

6. The method of claim 5 wherein said drug addiction is an addiction to nicotinic agonists.

7. The method of claim 5 wherein the drug addiction is an addiction to alcohol.

8. The method of claim 5 wherein the drug addiction is an addiction to cannabinoids.

9. The method of claim 5 wherein the drug addiction is an addiction to cocaine.

10. The method of claim 5 wherein the drug addiction is an addiction to amphetamines.

11. The method of claim 5 wherein the drug addiction is an addiction to opiates.

12. The method of claim 5 wherein the drug addiction is an addiction to barbituates.

13. The method of claim 5 wherein the drug addiction is an addiction to phencyclidine.

14. The method of claim 5 wherein the drug addiction is an addiction to hallucinogens.

15. The method of claim 5 wherein the drug addiction is an addiction to benzodiazepines.

16. The method of claim 5 wherein the drug addiction is an addiction to caffeine.

* * * * *